(12) United States Patent
Albert et al.

(10) Patent No.: US 8,124,332 B2
(45) Date of Patent: Feb. 28, 2012

(54) METHODS OF USING SIP-10, CD26 INHIBITORS AND CXCR3 LEVELS IN A SAMPLE TO ASSESS CLEARANCE OF INFECTION, RESPONSE TO INTERFERON THERAPY, AND TREATING CHRONIC INFECTIONS

(75) Inventors: Matthew Albert, Paris (FR); Armanda Casrouge, Draveil (FR); Jeremie Decalf, Paris (FR); Stanislas Pol, Juvisy sur Orge (FR); Arnaud Fontanet, Paris (FR); Mostafa Mohamed, Heliopolis Cairo (EG)

(73) Assignee: Institut Pasteur, Paris (FR)

( * ) Notice: Subject to any disclaimer, the term of this patent is extended or adjusted under 35 U.S.C. 154(b) by 0 days.

(21) Appl. No.: 12/533,388

(22) Filed: Jul. 31, 2009

(65) Prior Publication Data
US 2010/0040577 A1 Feb. 18, 2010

Related U.S. Application Data

(63) Continuation-in-part of application No. 11/855,238, filed on Sep. 14, 2007, now Pat. No. 7,674,578.

(60) Provisional application No. 61/085,102, filed on Jul. 31, 2008, provisional application No. 60/844,375, filed on Sep. 14, 2006.

(51) Int. Cl.
*G01N 33/573* (2006.01)
*A61K 45/08* (2006.01)

(52) U.S. Cl. ............................. 435/4; 435/7.4; 424/85.1
(58) Field of Classification Search ................... None
See application file for complete search history.

(56) References Cited

OTHER PUBLICATIONS

Proost et al. Blood 2001, vol. 98, pp. 13, pp. 3554-3561.*
Campanella et al. J. Biological Chemistry 2003, vol. 278, No. 19, pp. 17066-17074.*
Wiedeman et al, *Drug Discovery Today Therapeutic Strategies*, 2(2): 143-149 (2005).
McIntosh et al, *International Journal of Biochemistry & Cell Biology*, 38: 860-872 (2006).
Weber et al, *J. Med. Chem.* 47: 4135-4141 (2004).
Neville et al, *Cytokine & Growth Factor Reviews*, 8(3): 207-219 (1997).
Casrouge et al, The Journal of Clinical Investigation, 2011, vol. 121, No. 1, pp. 308-317 (w/ Supplementary Figure Legends) (http://www.jci.org).
Charles et al, The Jornal of Clinical Investigation, 2011, vol. 121, No. 1, pp. 25-27 (http://www.jci.org).

* cited by examiner

*Primary Examiner* — Bao Li
(74) *Attorney, Agent, or Firm* — Oblon, Spivak, McClelland, Maier & Neustadt, L.L.P.

(57) ABSTRACT

The present invention relates to methods for the treatment of infection, a disease, or a condition using CD26 (DPIV) inhibitors. The present invention also relates to an antibody that binds to the IP-10 protein and a method of monitoring the necessity for administering a CD26 inhibitor to a patient, comprising evaluating a level of sIP-10, a activity of CD26, and/or a level of CXCR3 cells in a sample.

10 Claims, 26 Drawing Sheets

The immune pathogenesis of hepatitis C virus

T cell response is essential in the outcome of the disease

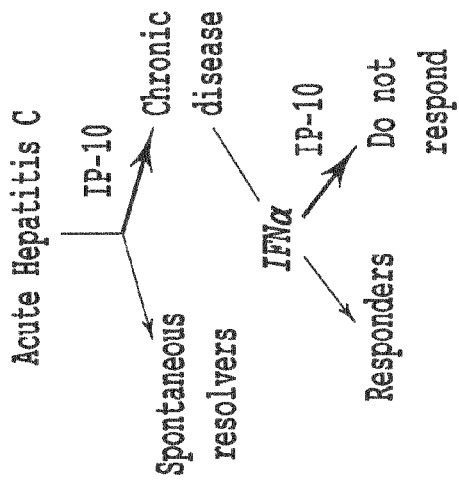
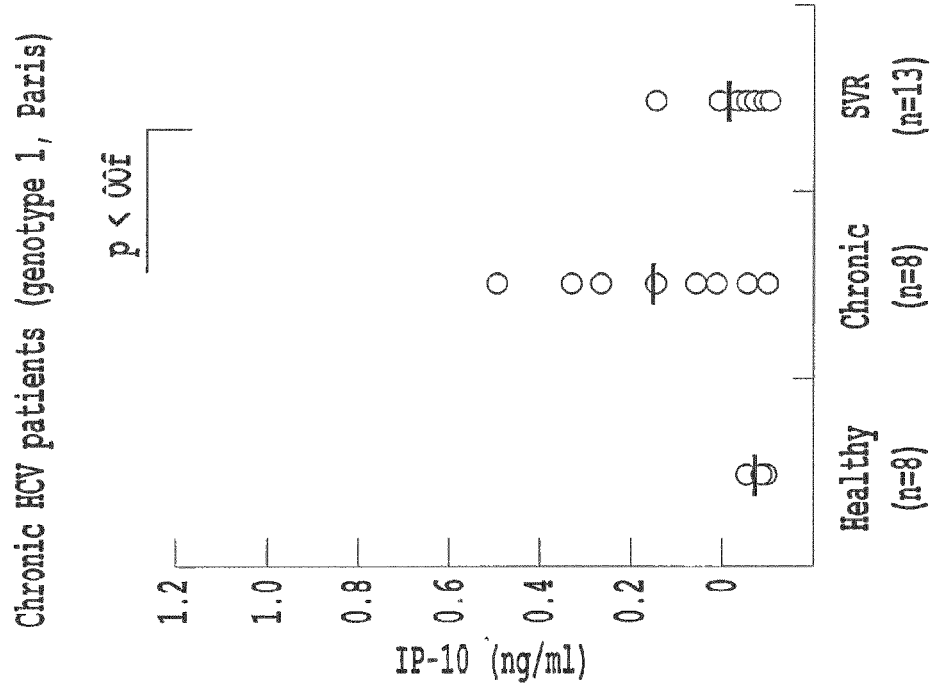
Fig. 2B
Fig. 2A

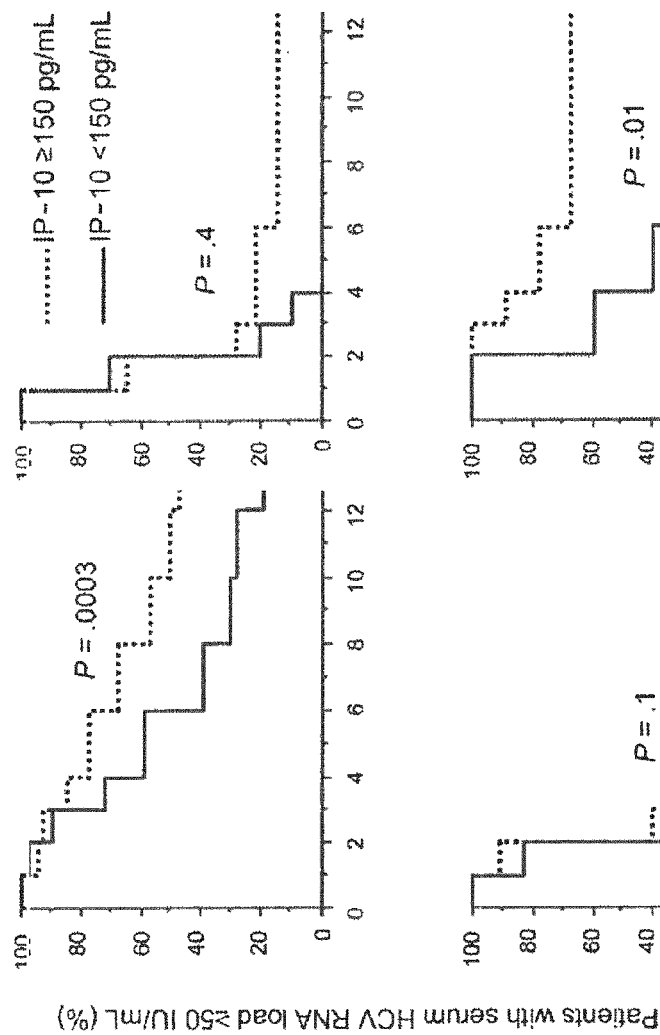

IP-10 = chemokine, it attacks activated T cells by creating a gradient
↑ Killer T cells clear viral infected cells X = Nonspecific
Y = Proline or alanine, slow release observed with Ser or Gly
Z = Cannot be Proline or hydroxyproline truncated IP-10 binds CXCR3 without signaling, competes for full length IP-10

*Fig. 7*

IP-10  vplsrtvrc tcisisnqpvnprslekleiipasqfcprv
eiiatmkkkgekrclnpeskaiknllkavskemskrsp (SEQIDNO:2)

Peptide 1: vplsrtvrc (SEQIDNO:5) for immunisation
Peptide 2 :   lrstvrc (SEQIDNO:6) for adsorption Rabbit for polyclonal antibodies
Mouse for monoclonal antibodies Figure 11
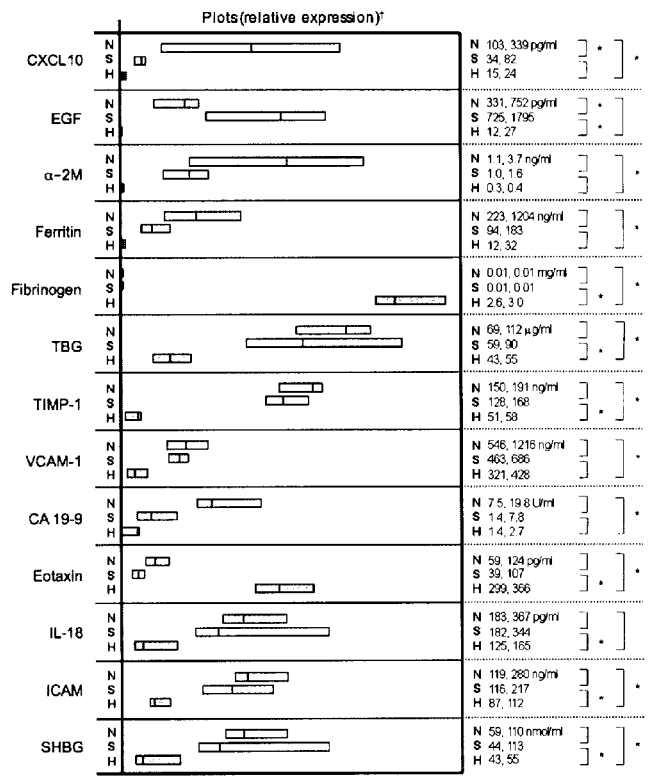
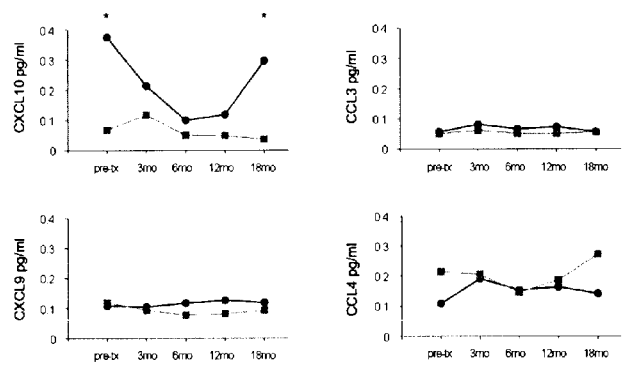

Figure 15
A
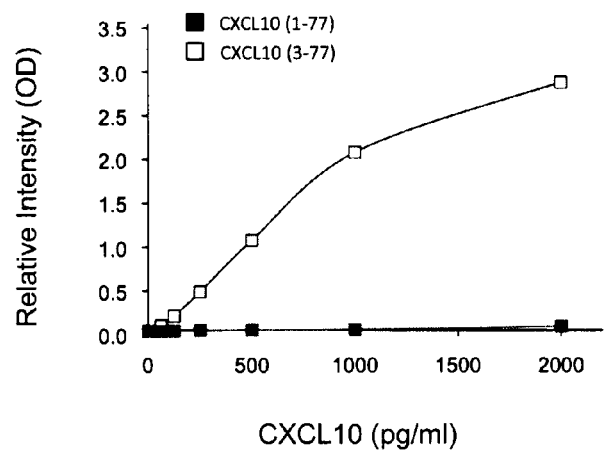
B
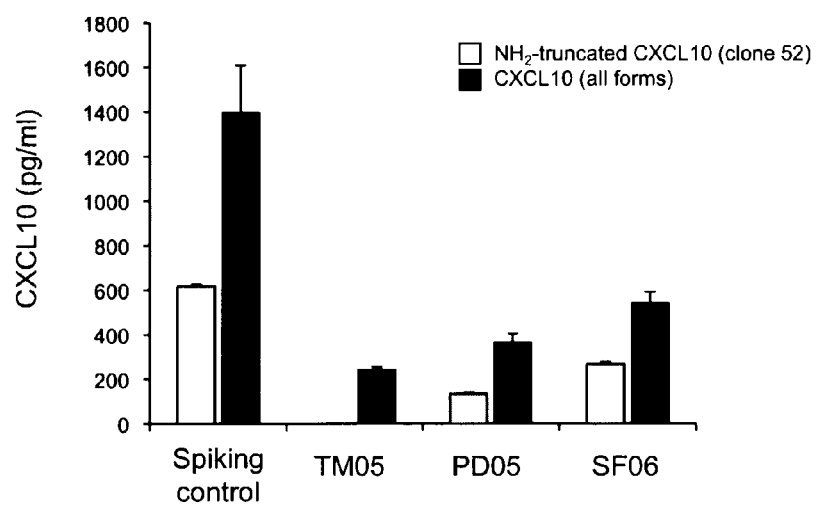

Figure 17
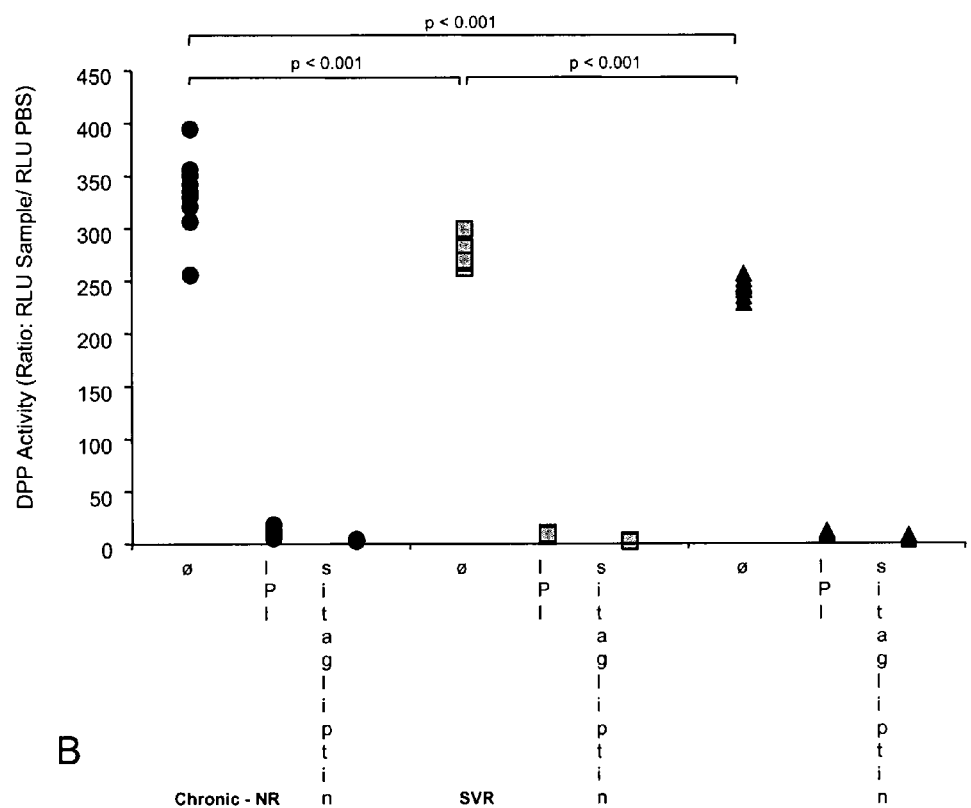
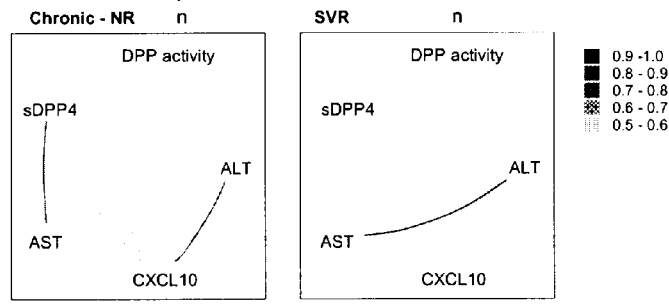

Figure 18
A
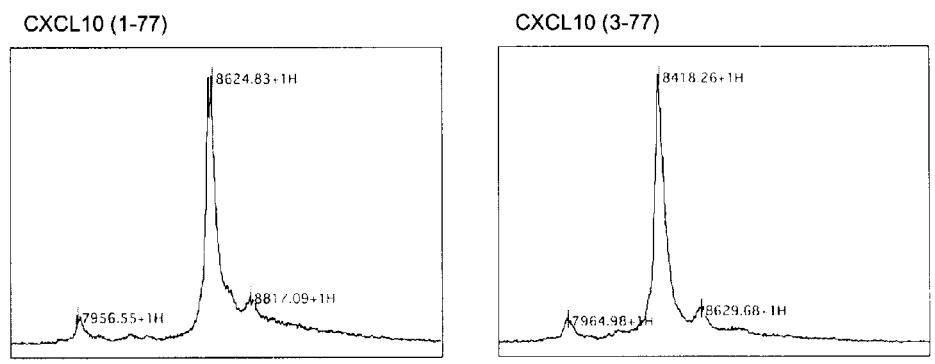
B
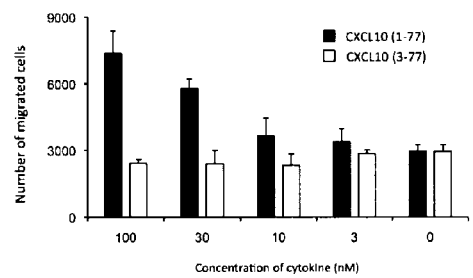
C
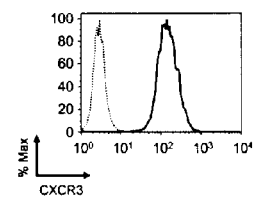
D
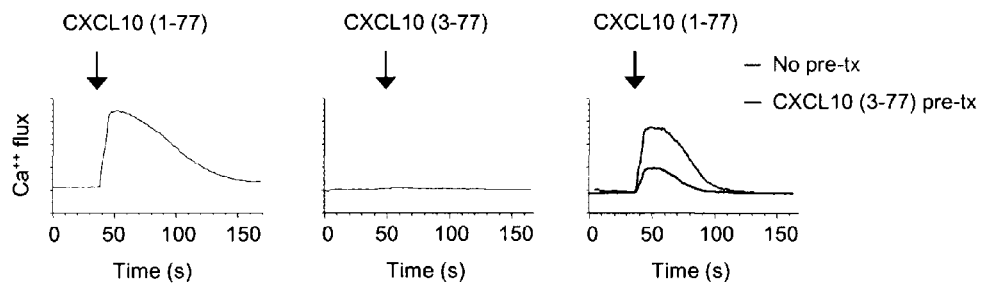

Figure 19
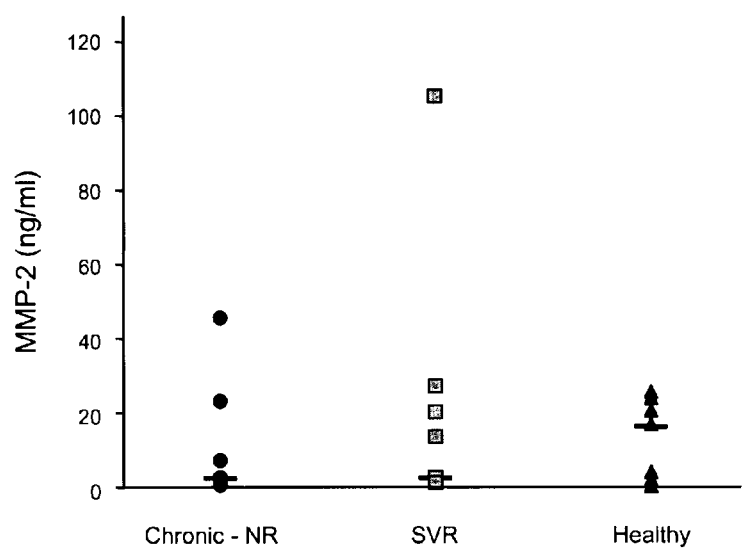
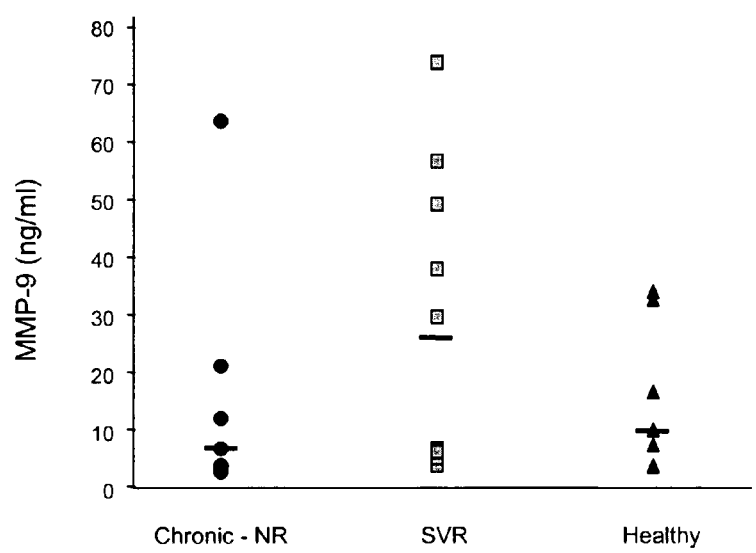

Figure 20
A
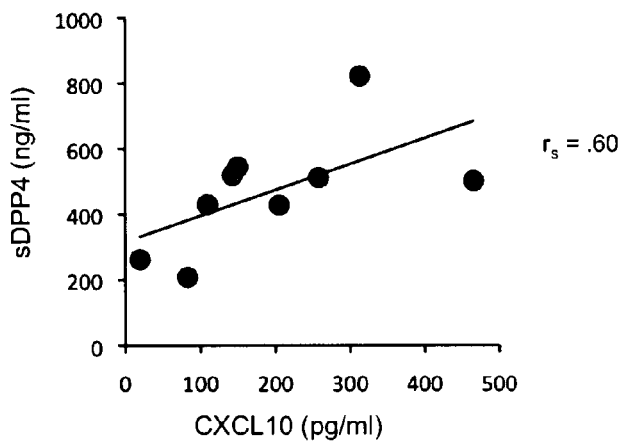
B
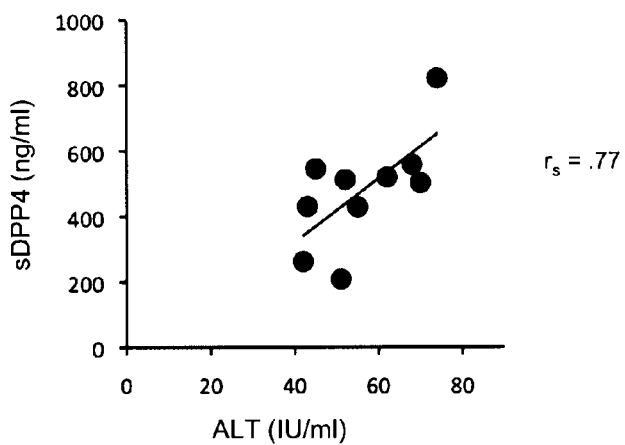
C
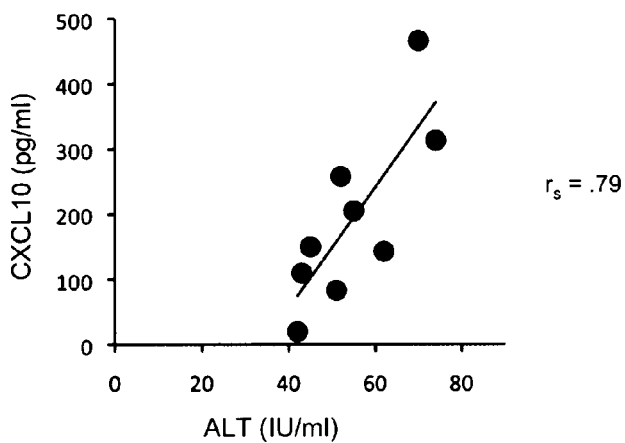

SEQUENCE LISTING

```
<160> NUMBER OF SEQ ID NOS: 6

<210> SEQ ID NO 1
<211> LENGTH: 98
<212> TYPE: PRT
<213> ORGANISM: Human
<220> FEATURE:
<221> NAME/KEY: mat_peptide
<222> LOCATION: (22)..(98)
<223> OTHER INFORMATION: Pro-IP-10

<400> SEQUENCE: 1

Met Asn Gln Thr Ala Ile Leu Ile Cys Cys Leu Ile Phe Leu Thr Leu
    -20                 -15                 -10

Ser Gly Ile Gln Gly Val Pro Leu Ser Arg Thr Val Arg Cys Thr Cys
 -5              -1   1               5                  10

Ile Ser Ile Ser Asn Gln Pro Val Asn Pro Arg Ser Leu Glu Lys Leu
            15                  20                  25

Glu Ile Ile Pro Ala Ser Gln Phe Cys Pro Arg Val Glu Ile Ile Ala
            30                  35                  40

Thr Met Lys Lys Lys Gly Glu Lys Arg Cys Leu Asn Pro Glu Ser Lys
        45                  50                  55

Ala Ile Lys Asn Leu Leu Lys Ala Val Ser Lys Glu Met Ser Lys Arg
 60                  65                  70                  75

Ser Pro

<210> SEQ ID NO 2
<211> LENGTH: 77
<212> TYPE: PRT
<213> ORGANISM: Human
<220> FEATURE:
<221> NAME/KEY: MISC_FEATURE
<222> LOCATION: (1)..(77)
<223> OTHER INFORMATION: Secreted full length protein

<400> SEQUENCE: 2

Val Pro Leu Ser Arg Thr Val Arg Cys Thr Cys Ile Ser Ile Ser Asn
 1               5                  10                  15

Gln Pro Val Asn Pro Arg Ser Leu Glu Lys Leu Glu Ile Ile Pro Ala
             20                  25                  30
```

```
Ser Gln Phe Cys Pro Arg Val Glu Ile Ile Ala Thr Met Lys Lys Lys
            35                  40                  45

Gly Glu Lys Arg Cys Leu Asn Pro Glu Ser Lys Ala Ile Lys Asn Leu
 50                  55                  60

Leu Lys Ala Val Ser Lys Glu Met Ser Lys Arg Ser Pro
 65                  70                  75

<210> SEQ ID NO 3
<211> LENGTH: 75
<212> TYPE: PRT
<213> ORGANISM: Human
<220> FEATURE:
<221> NAME/KEY: MISC_FEATURE
<222> LOCATION: (1)..(75)
<223> OTHER INFORMATION: 2 amino acids cleavage product after CD26
      treatment

<400> SEQUENCE: 3

Leu Ser Arg Thr Val Arg Cys Thr Cys Ile Ser Ile Ser Asn Gln Pro
 1               5                  10                  15

Val Asn Pro Arg Ser Leu Glu Lys Leu Glu Ile Ile Pro Ala Ser Gln
            20                  25                  30

Phe Cys Pro Arg Val Glu Ile Ile Ala Thr Met Lys Lys Lys Gly Glu
            35                  40                  45

Lys Arg Cys Leu Asn Pro Glu Ser Lys Ala Ile Lys Asn Leu Leu Lys
 50                  55                  60

Ala Val Ser Lys Glu Met Ser Lys Arg Ser Pro
 65                  70                  75

<210> SEQ ID NO 4
<211> LENGTH: 73
<212> TYPE: PRT
<213> ORGANISM: Human
<220> FEATURE:
<221> NAME/KEY: MISC_FEATURE
<222> LOCATION: (1)..(73)
<223> OTHER INFORMATION: 4 amino acid cleavage product after CD26
      treatment

<400> SEQUENCE: 4

Arg Thr Val Arg Cys Thr Cys Ile Ser Ile Ser Asn Gln Pro Val Asn
 1               5                  10                  15

Pro Arg Ser Leu Glu Lys Leu Glu Ile Ile Pro Ala Ser Gln Phe Cys
            20                  25                  30

Pro Arg Val Glu Ile Ile Ala Thr Met Lys Lys Lys Gly Glu Lys Arg
            35                  40                  45

Cys Leu Asn Pro Glu Ser Lys Ala Ile Lys Asn Leu Leu Lys Ala Val
 50                  55                  60

Ser Lys Glu Met Ser Lys Arg Ser Pro
 65                  70

<210> SEQ ID NO 5
<211> LENGTH: 9
<212> TYPE: PRT
<213> ORGANISM: Synthetic peptide

<400> SEQUENCE: 5

Val Pro Leu Ser Arg Thr Val Arg Cys
 1               5

<210> SEQ ID NO 6
<211> LENGTH: 7
```

```
<212> TYPE: PRT
<213> ORGANISM: Synthetic peptide

<400> SEQUENCE: 6

Leu Ser Arg Thr Val Arg Cys
1               5
```

METHODS OF USING SIP-10, CD26 INHIBITORS AND CXCR3 LEVELS IN A SAMPLE TO ASSESS CLEARANCE OF INFECTION, RESPONSE TO INTERFERON THERAPY, AND TREATING CHRONIC INFECTIONS

CROSS-REFERENCE TO RELATED APPLICATION

This application a Continuation-in-Part of U.S. application Ser. No. 11/855,238, filed Sep. 14, 2007, now U.S. Pat. No. 7,674,578, issued Jun. 8, 2010, which claims benefit of Provisional Application Ser. No. 60/844,375, filed Sep. 14, 2006, the entire contents of which are incorporated herein by reference. This application also claims benefit of Provisional Application Ser. No. 61/085,102, filed Jul. 31, 2008, the entire content of which is incorporated herein by reference.

BACKGROUND OF THE INVENTION

1. Field of the Invention

The present invention relates to methods for evaluating and predicting clinical outcomes in patients by measuring levels of protein expression as well as therapies using sIP-10 and its fragments. The present invention also relates to methods for the treatment of infections using CD26 (DPIV) inhibitors. The present invention also relates to methods of monitoring levels of CXCR3 cells in blood, a level of IP-10 and a CD26 activity for assessing patients as to clearing chronic infections and responding to IFN therapy and the necessity of administering CD26 inhibitors.

2. Description of the Background

Hepatitis C virus (HCV) is a significant health problem in that chronic hepatitis occurs in over 50% of infected individuals and may lead to the development of life threatening cirrhosis, hepatic cancer, as well as other sequellae. Chronic hepatitis is often treated with interferon α and/or β and other type I and III interferons that can also be administered in combination with ribavirin with varying levels of success depending on genotypes of the virus.

There are nearly 170 million HCV infected individuals worldwide (1). Many studies have explored the mechanisms by which the immune system is capable of mediating viral clearance (2). Although an HCV-specific humoral response is commonly seen, HCV-specific antibodies are not thought capable of conferring protection (3). Instead, protection in chimpanzees has been shown to correspond with HCV-reactive CD8$^+$ T cell responses. Similarly in humans, a tetramer analysis of successful resolvers indicates the presence of a high frequency of functional HCV-specific CD8$^+$ T cells (4). In addition, there is genetic data to support a role for NK cells based on the higher likelihood of KIR2DL3 and HLA-C1 individuals to clear infection (5). One thing is clear—cure is possible—20-40% of patients spontaneously resolve infection and 40-80% of chronically infected patients (numbers vary depending on viral genotype) that receive peg-IFN-$\alpha_2$/RBV therapy clear the virus and are sustained virologic responders (SVR) (6). Still for many, the virus manages to circumvent natural immunity and our therapeutic strategies, thus resulting in significant morbidity and mortality including liver cirrhosis or hepatocellular carcinoma.

To better define the distinct clinical outcomes of HCV infection many investigators have performed candidate molecule screens or transcriptional profiling in order to identify correlates of viral clearance. One molecule that has gained significant attention is CXCL10 (also known as interferon-gamma induced protein-10 or IP-10), an interferon- and TNFα-inducible chemokine that can be highly expressed by endothelial cells, keratinocytes, fibroblast, mesangial cells, astrocytes, monocytes, neutrophils and hepatocytes (7). In addition to HCV disease, it has been shown to be expressed in many Th1-type inflammatory diseases, often correlating with the target organ infiltration by T cells (8, 9). CXCL10 is a part of a family of α-chemokines that bind CXCR3, which also includes CXCL9 (also known as monokine induced by IFNγ or MIG) and CXCL11 (also known as IFN-inducible T cell α chemoattractant or I-TAC). While all three ligands are induced by IFN and bind the same receptor, there now exists substantial data to support their unique roles in disease pathogenesis. This is clearly evident in chronic HCV, wherein elevated levels of all three have been demonstrated, but only CXCL10 is predictive of a response to the therapy (10).

Regarding published studies of chronic HCV patients, at least five independent cohorts have demonstrated that baseline levels of CXCL10 are predictive of the failure to respond to HCV treatment (10-13). Specifically, this has been demonstrated in patients with genotype 1 and 4 HCV and in the largest study a negative predictive value of 79% was reported for genotype 1 patients (12). In addition, elevated levels of CXCL10 have been reported in patients co-infected by HCV/HIV (14, 15); and with HCV-associated cryoglobulinemia (16). In several of these reports, CXCL10 levels correlate with necroinflammatory activity, fibrosis stage and/or HCV viral load. However, none of the reports have resolved the paradox of why a pro-inflammatory chemokine, responsible for recruiting activated lymphocytes to the liver, is a negative prognostic marker for response to therapy.

The inventors hypothesized that CXCL10 in chronic HCV is catabolized and exists in an antagonist form, thus offering a rationale for its negative impact on treatment responsiveness. Such a mechanism of regulating a chemokine activity has been proposed for several chemokines. Pertinent in vivo examples include the degradation of monocyte chemoattractant protein-3 (MCP-3) by matrix metalloproteinase-2 (MMP-2), reported to be relevant to the pathogenesis of spondyloarthritis (17); and the cleavage of stromal cell derived factor-1 (SDF-1 or CXCL12) in HIV-associated neurodegeneration, also mediated by MMP-2 (18). Herein, the inventors provide direct evidence that the $NH_2$-terminal residues of plasma CXCL10 have been cleaved in HCV patients. Moreover, the inventors have found a correlation between the CXCL10 levels and the precursor frequency of CXCR3$^+$ cells in circulation, indicating in vivo that the chemokine gradient is non-functional. The inventors have investigated matrix metalloprotease (MMP) and dipeptidylpeptidase (DPP) family members as mediators of the truncation and evaluated a role of the enzyme dipeptidylpeptidase IV (DPP4 or CD26). Following from the observations, the inventors have found an important link between the metabolic complications and the chronic inflammation seen in HCV patients. The inventors have determined that DPP4 is a novel therapeutic target, inhibition of which results in the restoration of the CXCL10 gradient and allows for increased responsiveness to peg-IFN-$\alpha_2$/RBV therapy.

Even with interferon therapies, there are substantial side effects, and the costs of therapy are very high. Accordingly, there is a need to develop a way to assess when successful results can be expected in an individual patient with a particular IFN therapy.

Thus, an object of the invention is to provide a way in which to predict whether such therapies would be useful for treating certain patients and also a treatment of infections using CD26 (DPIV) inhibitors.

SUMMARY OF THE INVENTION

There exists a need to determine and predict clinical outcomes in patients with HCV. It is therefore an object of the invention to provide a means for evaluating (e.g., determining and/or predicting) clinical outcome for a patient suffering from a clinical condition or syndrome.

One aspect of the invention is using the short form of IP-10 (sIP-10) as a predictive marker for failure to clear HCV and failure to respond to IFN based therapy.

Another aspect is determining the total, long and short forms of IP-10 using antibodies that are specific for the long and/or short forms of IP-10.

Another aspect is to provide a treatment for infections, diseases, or conditions. In one embodiment a treatment of chronic Hepatitis C by administering a patient in need of the treatment an effective amount of a CD26 inhibitor to restore the chemokine gradient is provided. In a further aspect, predicting which patients will respond to therapy and improve upon the existing treatment of chronic HCV patients using combination therapy of interferon, ribavirin and CD26 inhibitors. In other aspect, CD26 inhibitors may be used as monotherapy to address some of the sequellae of chronic HCV, e.g., type II diabetes.

In another embodiment, a method of monitoring the necessity for administering CD26 inhibitors to a patient, comprising evaluating chemokine antagonism, is provided.

In a different embodiment, a level of CXCR3 in blood may be monitored.

In other aspects, the antibodies that distinguish between the short and long forms of IP-10 can be used to evaluate patients with chronic inflammation (e.g., infection, cancer, obesity, autoimmunity, graft vs. host disease).

BRIEF DESCRIPTION OF THE DRAWINGS

The patent or application file contains at least one drawing executed in color. Copies of this patent or patent application publication with color drawing(s) will be provided by the office upon request and payment of the necessary fee.

A more complete appreciation of the invention and many of the attendant advantages thereof will be readily obtained as the same becomes better understood by reference to the following detailed description when considered in connection with the accompanying drawings, wherein:

FIG. 2(A) shows graphical representation of IP-10 levels in 3 groups: healthy individuals, chronic HCV patients non-responsive and responsive (chronic-Genotype 1B) to therapy. About 50% of patients receiving IFN and Ribaviran for their chronic HCV will fail therapy. Multianylate profiling provided new biomarkers for chronic HCV infection. IP-10 as a negative predictive marker identifying a patients pre-treatment, who are prone to fail to archive a response to therapy, has been identified. (B) shows the immune pathogenesis of HCV and involvement of IP-10.

FIG. 3 shows results of previous studies (JID 2006:194, Ramero et al.) that have shown IP-10 to be a negative predictor for treatment in HCV genotypes 1 and 4.

FIG. 7 shows a strategy for generating antibodies to distinguish the long and truncated forms of IP-10.

FIG. 11(A-B) shows multi-analyte profiling of chronic HCV patients reveals CXCL10 as a negative predictor for response to therapy.

FIG. 15(A-B) shows a detection of $NH_2$-truncated CXCL10 in chronic HCV patients.

FIG. 17(A-B) shows that the elevated X-prolyl dipeptidylpeptidase activity in chronic HCV patients is mediated by DPP4.

FIG. 18(A-D) shows that the X-prolyl dipeptidylpeptidase DPP4 cleaves the two N-terminal amino acids of CXCL10, generating the antagonist CXCL10 (3-77) form.

FIG. 19(A-B) shows the plasma concentration of MMP2 and MMP9 in patients with chronic HCV. The plasma concentration of MMP2 (A) and MMP9 (B) was measured using luminex technology.

FIG. 20(A-C) shows the plasma concentration of sDPP4 and CXCL10 correlate with elevated liver enzymes in patients with chronic HCV. Plasma levels of sDPP4 and CXCL10 are plotted against ALT and AST levels.

DETAILED DESCRIPTION OF THE INVENTION

Figure 1:
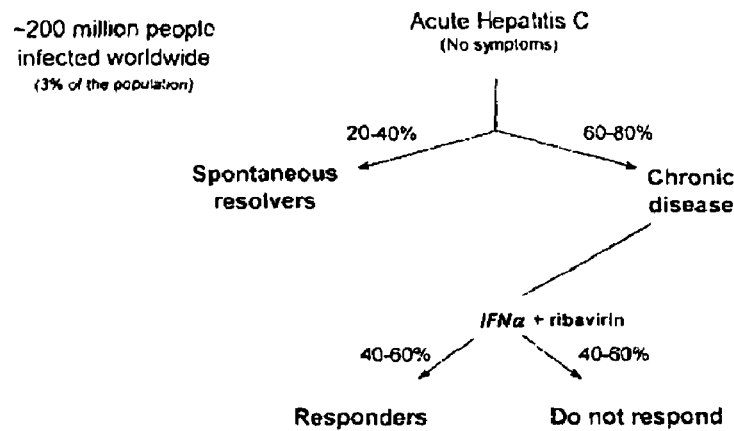
FIG. 1 provides an overview of the immune pathogenesis of hepatitis C virus.
Figure 4:
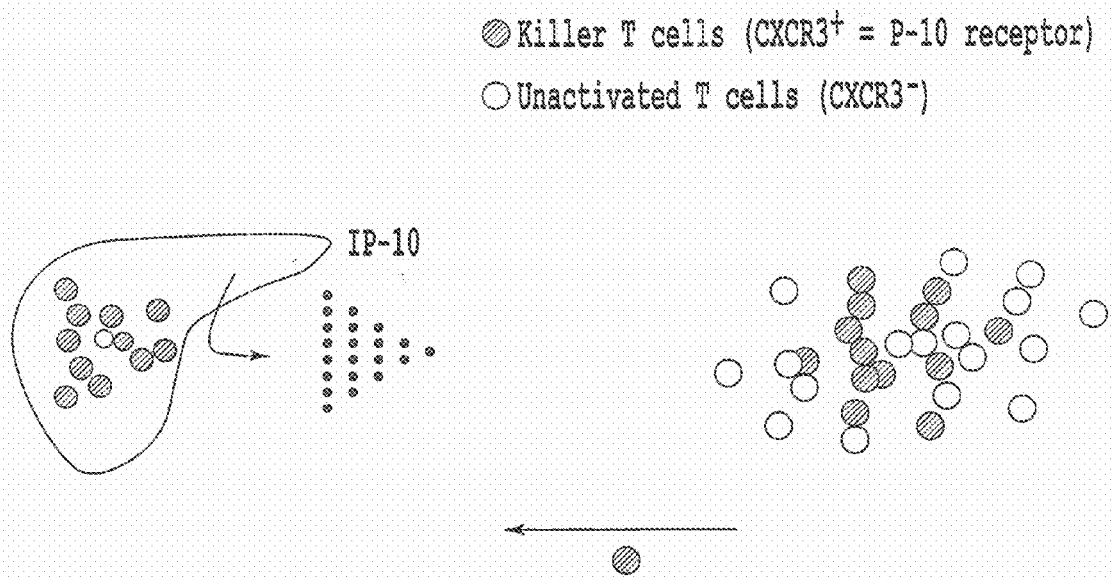
FIG. 4 An unexpected role for IP-10 in HCV disease pathogenesis. IP-10 is a chemoattractant for activated lymphocytes (expressing the IP-10 receptor, called CXCR3) and that in chronic HCV, the source is the liver. The expectation was that IP-10 should be acting to attract CXCR3 cells to the liver, thus enhancing viral clearance. Thus, it was non-obvious and counter-intuitive that IP-10 should be negative predictor of a response to a treatment.
Figure 5:
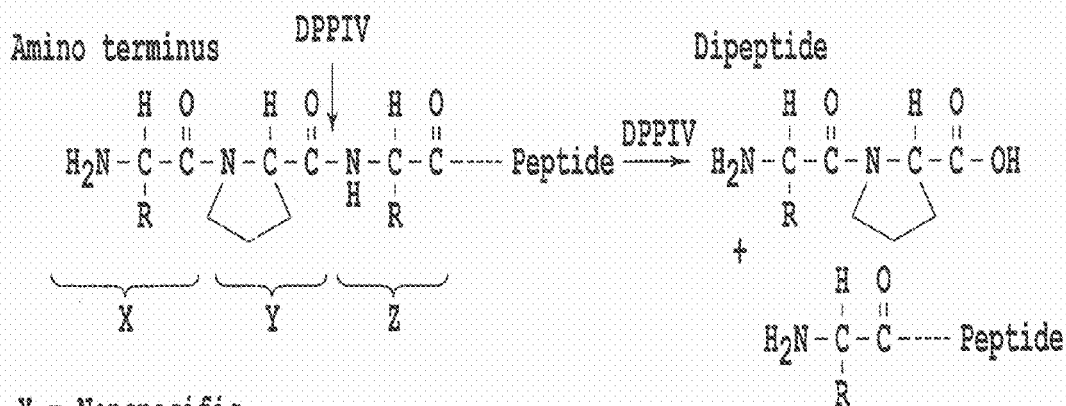
FIG. 5 illustrates that IP-10 is cleaved by CD26 (circulating dipetidyl peptidase IV) and generates an antagonist chemokine.
Figure 6B:
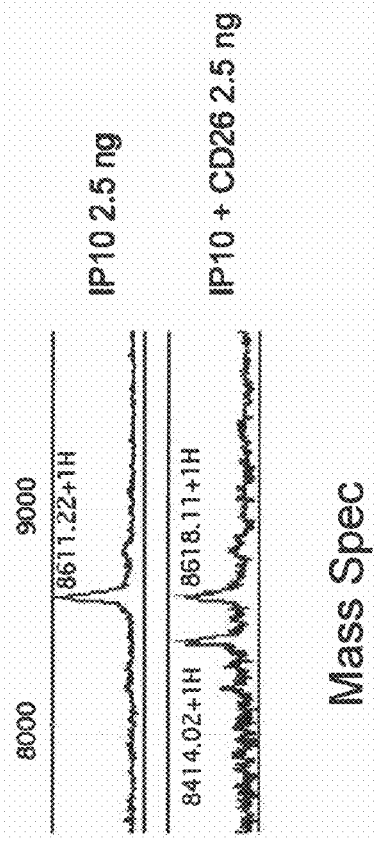
FIG. 6 shows western blot (A) and Mass spectroscopy to distinguish long and truncated IP-10 (B).
Figure 6A:
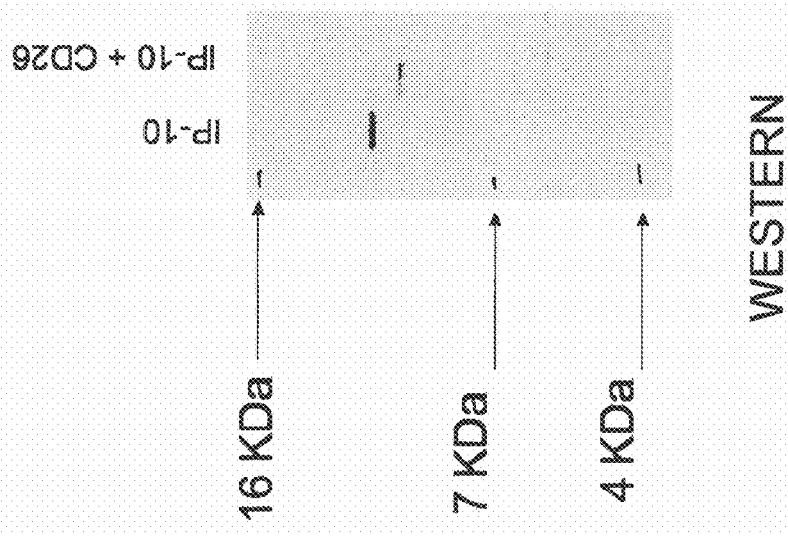
Figure 8:
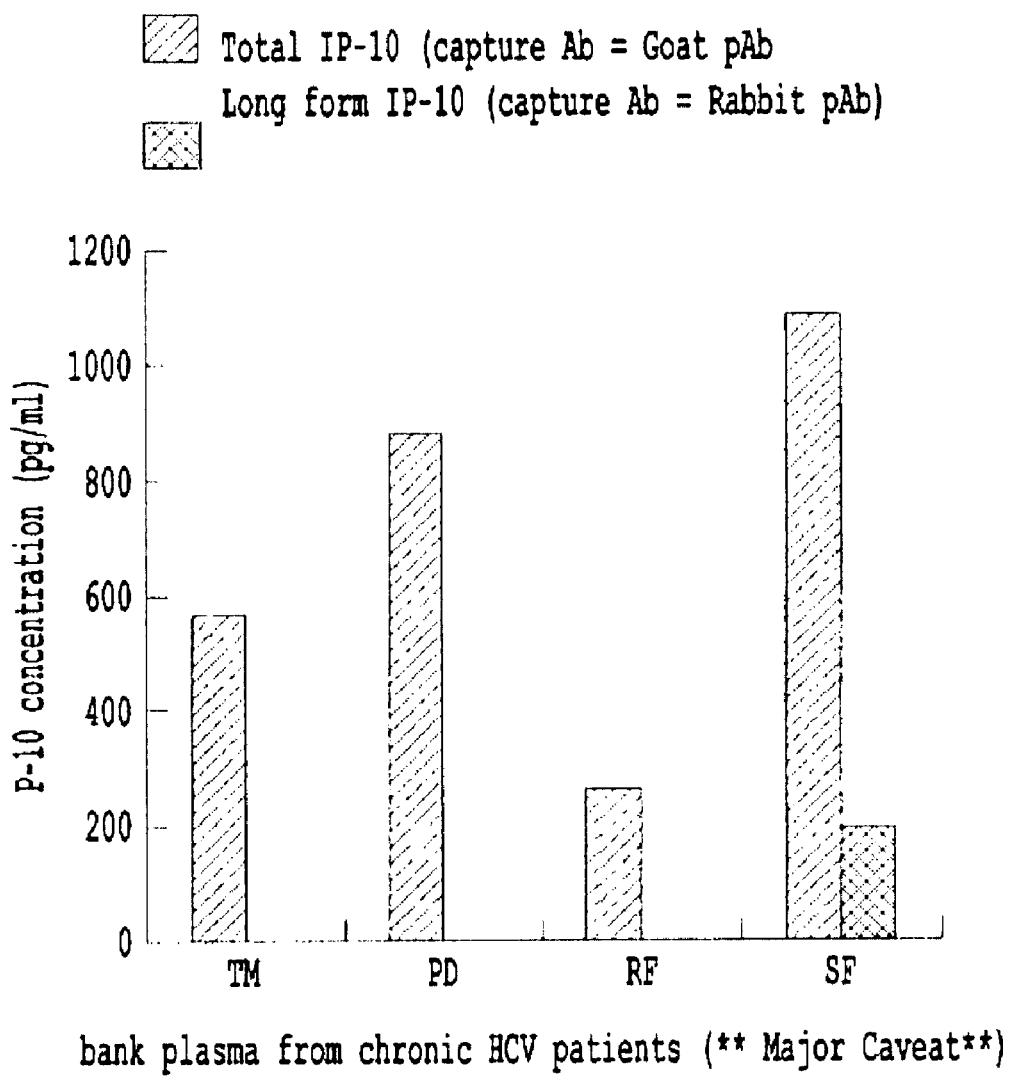
FIG. 8 shows data from four chronic HCV patients, where the dominant form circulating in their plasma is sIP-10. Total and long IP-10 was measured in plasma of chronicpatients after treatment with interferon and ribavirin. Non-responder (NR) patients have total IP-10 circulating in plasma, long IP-10 is not detectable. SVR (sustain viral responder) patients do not have a detectable IP-10 level in plasma.
Figure 9:
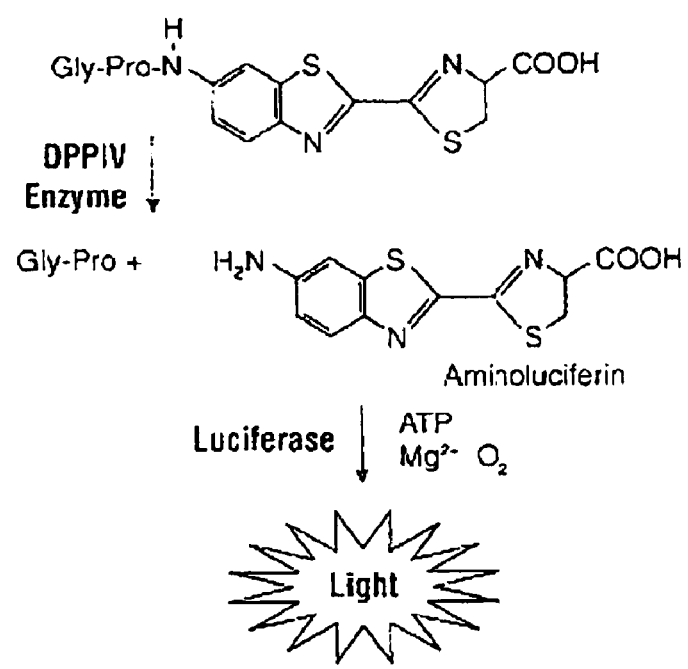
FIG. 9 shows the commercially available assay that can be used for monitoring bioactivity of the DPIV in patient plasma.
Figure 10:
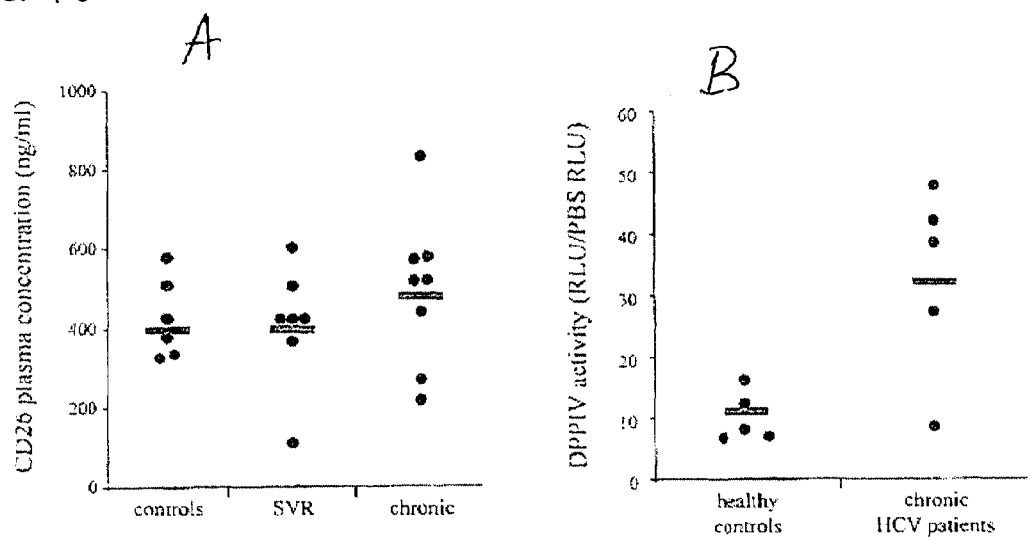
FIG. 10(A-B) shows that the concentration of CD26 in patients are not so different from healthy controls (see left graph). This contrasts the bioactivity studies. Chronic patients have a three-fold higher activity than the controls.

Unless specifically defined, all technical and scientific terms used herein have the same meaning as commonly understood by a skill artisan in chemistry, biochemistry, cellular biology, molecular biology, and medical sciences.

All methods and materials similar or equivalent to those described herein can be used in the practice or testing of the present invention, with suitable methods and materials being described herein. All publications, patent applications, patents, and other references mentioned herein are incorporated by reference in their entirety. Further, the materials, methods, and examples are illustrative only and are not intended to be limiting, unless otherwise specified.

The phrase "pre-selected gene(s)" refers to proteins that have been determined to be suitable in practice of the invention. Preferably, in accordance with practice of the invention, such proteins are selected where there is a correlation between the level of protein expression and the nature and extent of a disease state or other undesired condition.

Methods are provided for quantitating protein expression levels, and the measured levels are compared against reference populations. Deviations from the reference levels can be correlated with clinical outcomes. For example, the type and extent of a patient's response to a therapeutic intervention can be determined, or the prognosis for a patient's survival can be estimated. The protein levels can be measured in essentially any chosen body tissue or fluid.

IP-10 is CXC chemokine (NP 001556) and functions to recruit activated and memory lymphocytes to sites of inflammation. The secreted bioactive form (after cleavage of the signal peptide) is composed of a protein having 77 amino acids (positions 22-98). In situations where CD26 is expressed in an active state, IP-10 may be cleaved with the removal of its two N-terminal amino acids to a short form (termed sIP-10, amino acids 24-98). Importantly, sIP-10 has antagonist activities and repels activated and memory lymphocytes from sites of inflammation. IP-10 has previously been identified as a negative indicator for chronic HCV patients receiving the IFN/ribavirin treatment. This finding is somewhat counterintuitive as IP-I 0 is a proinflammatory molecule and should facilitate the priming of T cells by attracting CXCR3-cells (Th-1 cells) to the infected organ.

The inventors have identified IP-10 as a negative prognostic indicator for chronic HCV patients receiving treatment. The observation that IP-10 correlates with failure to spontaneously clear the virus as well as with failure of chronic HCV patients to respond to therapy suggests a common mechanism for non-responsiveness (and possibly, a common mechanism by which patients successfully resolve infection, whether it be natural or therapeutic).

The inventors have identified a positive correlation between the IP-10 levels in patients and the number of CXCR3 cells in circulation. This too was counter intuitive as IP-10 in the tissue should result in the homing of CXCR3 ((the sole receptor for IP-10) and a depletion of CXCR3 cells from the blood. The resolution of these paradoxical observations comes from the prediction that IP-10 is acting as an antagonist. Indeed, the inventors have confirmed that the two N-terminal amino acids of IP-10 are cleaved by CD26 and, in turn the short form inhibits CXCR3 by acting as a dominant negative.

The inventors have analyzed the relationships of IP-10 and HCV and have discovered that IP-10 is a negative predictive marker for clearance of hepatitis C virus (HCV). This has been demonstrated, for example, in a cohort of chronically infected HCV patients with genotype 1 virus (Paris cohort). Notably, the study compared chronically infected patients and sustained virologic responders, but data from other groups (Butera et al, Blood, 106(4):1175 (2005)) support the inventors' findings. This observation has been confusing for the field as it is counter-intuitive because IP-10 is considered a pro-inflammatory molecule and should facilitate the efficient priming of anti-HCV specific T cells.

Thus, the invention and the solution to this problem are based on the identifying by the inventors a positive correlation between the IP-10 levels in patients and the absolute number of CXCR3 positive cells in circulation. It has been suggested in the literature that IP-10 may be cleaved by CD26 (also called DPPIV, dipeptidyl peptidase IV), resulting in the generation of a short form of IP-10 (sIP-10) that acts as an antagonist of CXCR3 (De Meester et al, Immunology Today, 20(8):367 (1999)). sIP-10 is implicated in the failure of chronically infected HCV patients to respond to interferon therapy. Additional applications may include evaluation of patients with chronic inflammation (e.g. cancer, obesity, autoimmunity, graft vs. host disease). Specific applications should be focused on diseases in which IP-10 and/or CD26 have been shown to be elevated (e.g., melanoma, type II diabetes, autoimmune vasculitis). IP-10 is implicated in every chronic infection, autoimmunity andncer. Also, there are related enzymes such as FAP that cleaves IP- and is upregulated in many cancers such as melanoma. Neville et al. (Cytokine and Growth Factor Review, 8(3):207-219 (1997)) describe the immunobiology of IP-10. This cytokine is implicated in various biological systems, e.g., cell development, cell division, cell differentiation, chemotaxis, cell adhesion, cell cytolysis, angiogenesis, anti-tumor mechanisms, and regulation of feeding (see, e.g., Table 3 of Neville et al.).

Thus, as used herein, it is understood that sIP-10 means a short form of IP-10 that has been cleaved by CD 26 and portions thereof. sIP-10 lacks some N-terminal residues but always conserves the C-terminal residues which are useful to the binding of the truncated cytokine to its CXCR3 receptor. For example, sIP-10 has an amino acid sequence shown as SEQ ID NO:3. In another embodiment, the sIP-10 has the sequence of RTVRC TCISISNQPV NPRSLEKLEI IPASQFCPRV EIIATMKKKG EKRCLNPESK AIKNLLKAVS KEMSKRSP (SEQ ID NO:4). These sequences can be used as well as fragments thereof having at least 10, 15, 20, 25, 30, 35, 40, 45, 50, 55, 60, 65, 70 and 75 amino acids thereof, as well as all values and ranges there between.

Therefore, sIP-10 is a clinically important predictive marker for failure to clear HCV and failure to respond to the IFN therapy. This represents an important and medically useful discovery as we have the ability to determine prior to treatment, which patients will fail therapeutic treatment, thus saving them from up to a year of an expensive treatment with significant side effects (e.g., major depression). Of note, ~50% of genotype 1 patients fail to clear virus in response to IFN therapy. Furthermore, the introduction of such a diagnostic tool may assist physicians in determining responsive patients, thus pushing them to treat earlier with potentially more impact in avoiding the long-term sequella of HCV (e.g. cirrhosis, hepatocellular carcinoma).

Thus, the short (truncated) form of IP-10 (sIP-10) can be used as an improved predictive marker for failure to clear HCV and failure to respond to IFN therapy. It also permits optimal use of resources, an important factor in the treatment of HCV in regions such as Egypt and other developing countries. Further, CD26 can also be used as a therapeutic target. The CD26 inhibitors can be used to treat HCV patients with a combination therapy with Peg-IFN$\alpha_{2A}$/Ribavirin, Peg-IFN$\alpha_{2B}$/Ribavirin or a combination thereof. Other type I and III IFNs can be also used.

While there are many approaches aimed at increasing the numbers of antigen-specific T cells, we believe that this is not the problem in HCV disease pathogenesis. The real issue is getting the T cells to the right place—the liver. There are no current therapies aimed at reversing the effects of chemokine antagonism. Moreover, there are few approaches for HCV that are aimed at immune modulation: instead, most efforts are focused on inhibiting the vital protease and/or other viral proteins. While effective, such approaches are not yet available and seem to early carry serious side effects.

In one embodiment, a method of treating infections, diseases, or conditions composing administering to a patient in need thereof, an effective amount of a CD26 inhibitor to restore the chemokine gradient, thereby treating the infection, disease, or condition, is provided. The patient can be infected with hepatitis C virus. The patient can also be chronically infected with HCV.

Total, long and short (truncated) IP-10 can be determined utilizing polyclonal (rabbit) and monoclonal (mouse) antibodies that are specific for the long form of IP-10. In an added embodiment, in vivo IP-10 activity can be assessed by using CXCR3 cells as a surrogate for IP-10 activity. Flow cytometry can be used to measure the relative amount of CXCR3 cells in the peripheral blood of patients throughout their treatment. This will serve as a reflection of the ability of activated T cells and B cells to respond to a gradient of IP-10 (keeping in mind that there exist other CXCR3 agonists). In another added embodiment, a dipeptidyl peptidase IV activity can be measured in patient plasma, which can correlate to the IP-10 cleavage.

In these analysis, it is preferred to inactivate the plasma DPPIV activity, thus preventing an extra-corporeal cleavage of IP-10. Collections are thus preferably performed with protease inhibitors. For example, one such commercially available sample collection tube is BD™ P700 but other such BD™ 100 are also sufficient to preserve IP-10 in its circulating form.

In one embodiment, antibodies specific for the long form of IP-10 to evaluate the amount of long vs. short form of IP-10 are generated. Such antibodies that distinguish full-length IP-10 from short (truncated) form of IP-10, were generated by immunization of rabbits with a synthetic peptide coupled to KLH; (VPLSRTVRC (SEQ ID NO:5) corresponding of the $NH_2$ terminal of the full-length IP-10 protein). Immunoglobulines G (IgG) can then be purified in two steps by chromatography affinity: the first step is a positive selection of IgG that recognize the long peptide. The second step is depletion of IgG that recognize the shorter peptide LSRTVRC (SEQ ID NO:6) common to short and full-length form of IP-10. Purified antibodies are specific to full-length IP-10. The same strategy can be used to obtain polyclonal antibodies from different species (e.g., goat, chicken, and others). Monoclonal antibodies may also be derived from mice after immunization with the long peptide. After verifying the presence of antibody production in the serum, hybridomas are produced and cloned. The hybridoma screening can be made by direct ELISA with both, the long and short peptides, and the full-length and short form of recombinant IP-10 coated directly in ELISA plate. Then antibodies from hybridomas specific of the full-length can be purified. Validation of polyclonal antibodies can be performed by direct and by sandwiches Elisa assays against short and full-length IP-10 form. SIP-10 can be generated by following in vitro digestion of recombinant full-length IP-10 by recombinant CD26. The two $NH_2$ amino-acids, Valine and Proline are truncated from the full-length.

Using these distinguishing antibodies, IP-10 can be detected in biological fluids, for example, using an ELISA assay to specifically detect the full-length IP-10. As IP-10 binds to heparin, heparin crosslinked to agarose beads via amide bonds can be used to concentrate IP-10 from plasma. IP-10 can be eluted with NaCl 1M. To avoid or at least minimize ex vivo truncation of IP-10 in biologic samples, inhibitors of CD26 can be added into collection tubes. The HuCAl (Human Combinatorial Antibody library) technology allows to generate in vitro a 1.5 billion human antibodies candidates library. An automated panning process is used: the peptides specific of long and short forms of IP-10 are immobilized in 384-well microplate for screening against antibody-displaying phage library. Specificity of antibodies is then verified by ELISA.

To generate the short (truncated) IP-10 form, the full length IP-10 sequence (vplsrtvrctcisisnqpvnprslekleiipasqfcprveiiatmkkkgekrclnpeskaiknllkavskemskrsp, SEQ ID NO:2) can be incubated with CD26 at 25-37° C. to generate the short form (lsrtvrctcisisnqpvnprslekleiipasqfcprveiiatmkkkgekrclnpeskaiknllkavskemskrsp, SEQ ID NO:3). CD26 is a known protein, with a cloned sequence (e.g., from mammals such as human and mouse). Resolution of IP-10 and sIP-10 can be accomplished by Western blotting or by MALDI-TOF-MS as is known in the art.

Chemokine antagonism is responsible for resistance to IFN$\alpha_{2a}$/Ribavirin therapy in patients with chronic HCV. Determining the levels of the antagonist form of IP-10 will serve as a predictive marker for responsiveness to therapy: and treatment with an inhibitor of CD26 (also known as dipeptityl peptidase IV) can be used to decrease the antagonist form of IP-10 and help re-direct HCV-specific T cells to the liver. Thus, sIP-10 can be used for studying the failure of chronically infected HCV patients to respond to interferon therapy. Thus, the invention provides means to improve treatments of Hepatitis C in patients (mammalian, generally with humans, preferred) and, in one embodiment, such is accomplished by predicting which patients will respond to therapy: and improve upon the existing treatment of chronic HCV patients using combination therapy. Such combination therapy can employ existing HCV treatments with interferons, e.g., interferon α (preferably IFN $\alpha_{2A}$ and IFN $\alpha_{2B}$) and ribavirin with CD26 (DPIV) inhibitors as discussed herein. Other type I and III interferons can be used. One, two or more interferons can be used. The various inhibitors currently undergoing animal and human testing vary in both potency and length of action. For example, Novartis, Merck and Prosidion (PSN9301) compounds are currently in phase III trials and clinical data are likely to become available in the near future. Various CD26 (DPIV) inhibitors are also described in McIntosh et al., *Applications of dipeptidyl peptidase IV inhibitors in diabetes mellitus*, International Journal of Biochemistry & Cell Biology, 38(5-6): 860-872 (May-June 2006), e.g., a large number of DPIV inhibitors have been described and their structures and characteristics have been succinctly reviewed ([Augustyns et al., 1999], [Evans, 2002] and [Weber, 2004]; Wiedeman and J. M. Trevillyan, Dipeptidyl peptidase IV inhibitors for type 2 diabetes and metabolic syndrome, Drug Discovery Today Therapeutic Strategies, 2(2): 143-149 (2005)). The majority of inhibitors fall into one of three main classes (FIG. 3 of McIntosh et al.): (1) Reversible product analogs (e.g. pyrrolidine, thiazolidine), including P32/98 and PSN9301 (Probiodrug, Prosidion) and MK-432 (Merck); (2) Covalently bound product analogs (e.g. Cyanopyrrolidide), including NVP DPP 728 and LAF 237 (Novartis) and BMS-477118 (Bristol-Myers Squibb); and (3) Reversible non-peptide heterocyclic inhibitors (e.g. xanthine, aminomethylpyrimidines), including xanthin (NOVO) and aminomethylpyridine (Roche).

In other embodiments, the antibodies that distinguish between the short and long forms of IP-10 can be used to evaluate patients with chronic inflammation (e.g., cancer, obesity, autoimmunity, graft vs. host disease). Specific applications can be focused on diseases in which IP-10 and/or CD26 have been shown to be elevated (e.g., melanoma, type I1 diabetes, autoimmune vasculitis).

CD26/dipeptidyl-peptidase IV (DPP-IV) inhibitors include, amino boronic dipeptide talabostat (PT-100), Ile-Pro-Ile (Diprotin A), alanyl pyrrolidine, isoleucyl thiazolidine, and N-valyl prolyl, and O-benzoyl hydroxylamine. One such inhibitor sold as a treatment for type 2 diabetes is JANU- VIA™ (sitagliptin phosphate). One, two or more CD26/dipeptidyl-peptidase IV (DPP-IV) inhibitors can be used.

Other such inhibitors are known and described in U.S. Pat. No. 4,935,493, "Protease Inhibitors"; U.S. Pat. No. 5,462,928, "Inhibitors of Dipeptidyl-aminopeptidase Type IV"; U.S. Pat. No. 5,543,396, "Proline Phosphonate Derivatives"; U.S. Pat. No. 5,296,604, "Proline Derivatives and Compositions for Their Use as Inhibitors of HIV Protease"; PCT/US92/09845, "Method for Making a Prolineboronate Ester". Representative structures of the transition-state analog-based inhibitors Xaa-Boro-Pro, include Lys-boroPro, Pro-boroPro, Val-boroPro and Ala-boroPro in which "boroPro" refers to the analog of proline in which the carboxylate group (COOH) is replaced with a boronyl group (B) $(OH)_2$. Compounds as described in U.S. Pat. No. 6,100,234. One, two or more inhibitors can be used. All of the preceding patents and patent applications are incorporated herein by reference.

One embodiment of the invention is to assess the ability of a patient to clear HCV from circulation and/or the body. In another embodiment, the effectiveness of interferon therapy can be assessed.

According to these embodiments, it is possible to assess these indices by determining the expression levels of sIP-10. In these embodiments, one can assess the expression and effects by comparing the expression level of sIP-10 to a set of reference expression levels predictive of a patient's ability to clear HCV. Likewise, an increased expression of sIP-10 relative to a reference expression standard is indicative of a decreased ability to clear HCV.

In another embodiment, a method of monitoring the necessity for administering a CD26 inhibitor to a patient, comprising evaluating chemokine antagonism in a sample is provided. In a different embodiment, a level of CXCR3 in blood of the patient and/or a level of $NH_2$-terminal truncation of IP-10 protein can be also monitored/evaluated for assessing the necessity for administering a CD26 inhibitor to a patient.

Since the effectiveness of IFN therapy is not limited to an HCV infected patients, the methods can be carried out in patients not infected or not known to be infected.

A patient not infected with HCV who may benefit from this methodology may be a patient with a disease in which IFN is a normal course of therapy as known in the art.

An "individual" or "patient" which may be subjected to the methodology described herein may be any of mammalian animals including human, dog, cat, cattle, goat, pig, swine, sheep and monkey. Humans are preferable.

A "sample" is a biological sample such as blood, serum, plasma, lymph, and tissue. The "sample" may also be pre-treated, for example, by homogenization, extraction, enzymatic and/or chemical treatments as commonly used in the field.

The preparation and/or isolation of protenacious material from a sample for analysis are also well known in this field.

Measuring the levels of sIP-10 expression in a sample is easily undertaken by one knowledgeable in this field. Non-limiting examples include, western-blot analysis, ELISA assays, immuno-reactivity assays, column assays using fluorescence, antibodies and radiolabeled markers to detect. Automated manners of performing the analysis, for example, using a computer processor can also be used.

The inventors developed the first method of detecting long form of IP-10. No detection system to date has been described for the detection of long form IP-10 and the determination of the amount of sIP-10 in a sample. This novel tool supports a method for predicting responsiveness to therapy in chronically infected HCV patients. Other applications may exist. This new tool solves the problem of determining the ratio of long to short form of IP-10. It has immediate use in a prospective observational study for developing predictive markers in HCV patients.

Inhibiting CD26 and/or providing a short form of IP-10 as an agonist of full length IP10 is part of the invention. The polypeptides can be naturally obtained, obtained from recombinant sources and/or synthesized chemically, the procedures for which are known in the field. Administration can be any suitable route, for example, intravenously, intranasally, peritoneally, intramuscularly, orally and other conventional methods. An active compound can be mixed and/or carried with one or more liquid and/or solid pharmaceutically acceptable carriers, ingredients and/or excipients.

High Levels of Plasma CXCL10 Correlates with Failure to Respond to Peg-IFN-$\alpha_2$/RBV Therapy In order to identify biomarkers for response to therapy, the inventors have analyzed chronic HCV patients with plasma samples taken prior to, during and following their 48-week course of peg-IFN-$\alpha_2$/RBV. Multi-analyte profiling was performed on 84 selected molecules involved in inflammation, liver function and metabolism. The inventors performed a Kruskal-Wallis analysis of variance, comparing patients who failed to respond to therapy (non-responders, N–n=9), those who cleared the virus (sustained virologic responders, S–n=13) and healthy individuals (H–n=7) (FIG. 11). Of the 84 analytes, only CXCL10 and epidermal growth factor (EGF) showed a statistically significant difference between the non-responders and SVRs at the pre-therapy time-point (FIG. 11A). Eleven other analytes were found to distinguish HCV infected patients from healthy donors with most of them being involved in liver inflammation ($\alpha$-2M, ferritin, fibrinogen, thyroid binding globulin, IL-18, ICAM and SHBG) (19-22) and tissue remodeling (TIMP and VCAM-1) (23). While CXCL10 was elevated pre-therapy in treatment non-responders, levels were reduced during the course of therapy, again returning to high plasma levels six months post-therapy (FIG. 11B). In contrast to CXCL10, the inventors observed no differences in the plasma concentration of CXCL9, a second CXCR3 ligand, nor did the inventors see differences in CCL3 or CCL4, two ligands for CCR5 with the latter molecule also being an interferon-induced chemokine.

NH-$_2$-Truncated CXCL10 is the Dominant Form Circulating in Chronic HCV Patients Several independent studies have previously identified CXCL10 as a biomarker for chronic HCV patients (10-13), however, none of the published reports account for why a pro-inflammatory Th1-type chemokine might be a negative predictor for response to therapy. The inventors hypothesized that CXCL10 is present in an antagonist form in chronic HCV patients, thus accounting for it correlating with treatment failure. Briefly, chemokines act by binding to G-protein coupled receptors and mobilization of intracellular $Ca^{++}$, which resulting in receptor internalization and the initiation of signaling pathways that facilitate chemotaxis. For the CXC class of chemokines, binding to, and activation of the receptor is thought to be a two-step process. First, the core of the ligand binds the outer surface of the receptor; a second step involving the re-orientation of the flexible N-terminal tail of the protein allows binding to a distinct domain within the receptor (24). Post-secretion modification of CXCL10 has been described, including C-terminal cleavage by metal metalloproteinase 9 (MMP9 or gelatinase B) and citruillination by peptidylarginine deiminase (PAD), both of which leave the protein in an agonist state (25, 26). Also reported is the N-terminal cleavage of two amino acids by members of the X-prolyl dipeptidylpeptidase (DPP) family, the most characterized being dipeptidylpeptidase IV (DPP4 or CD26)(27). DPP4 has been shown to cleave several chemokines, including members of the α-chemokine family (28, 29).

In order to test the hypothesis, it was necessary to generate novel reagents. First, recombinant full length CXCL10 (1-77) was exposed to recombinant DPP4 and cleavage was monitored by SELDI mass spectroscopy (FIG. 18A). These data support the cleavage of two amino acids for the generation of an $NH_2$-terminal truncated CXCL10 (3-77). Next, the inventors performed in vitro studies confirming that CXCL10 (1-77) but not CXCL10 (3-77) is capable of: (i) directing the migration of $CXCR3^+$ cells (FIG. 18B); (ii) mediating receptor internalization in primary PBMCs (not shown); and (iii) triggering a $Ca^{++}$ flux in CHO cells transfected with a CXCR3 expressing plasmid (FIGS. 18C, 18D). Finally, the inventors have demonstrated that pre-treatment with CXCL10 (3-77) antagonized CXCL10 (1-77) induced $Ca^{++}$ mobilization (FIG. 18D). These data indicate that CXCL10 (1-77) is a DPP4 substrate and that $NH_2$-terminal cleavage results in a competitive antagonist form of CXCL10. To date, however, there has been no in vivo evidence to support a role for CXCL10 antagonism in disease pathogenesis. In part, the challenge in establishing in vivo evidence of this mechanism of immune regulation is due to the inability to discriminate the two forms of the chemokine by a sensitive, immune-based assay.

Figure 12A:
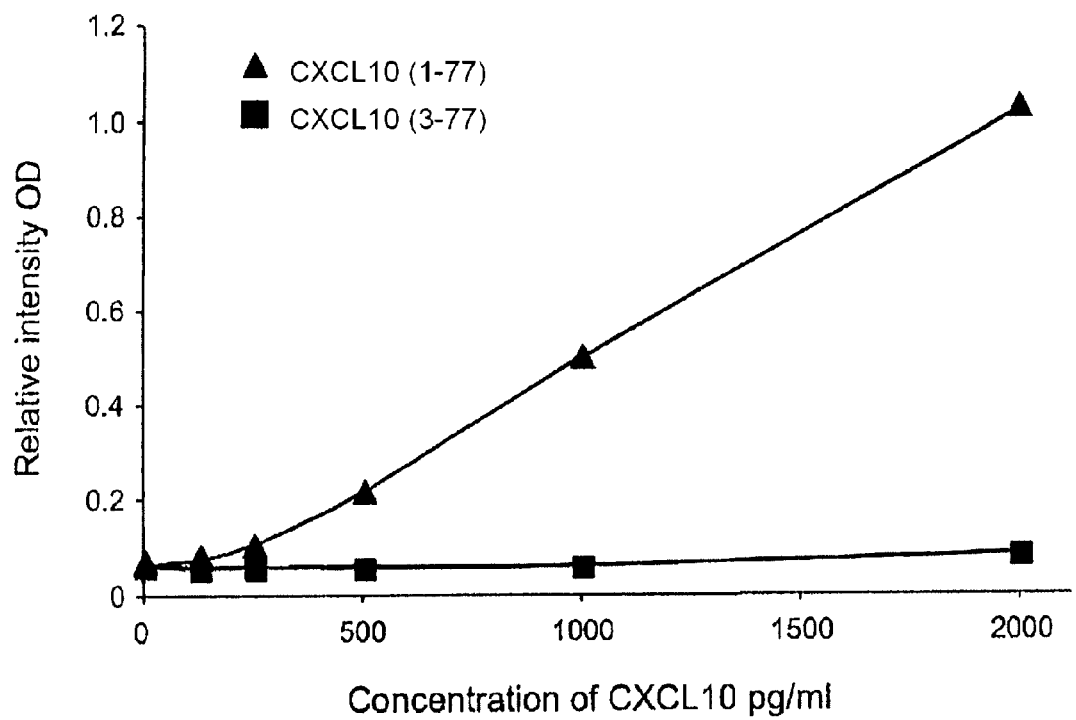
FIG. 12(A-F) shows evidence for $NH_2$-terminal truncation of CXCL10 in chronic HCV patients.
Figure 12B:
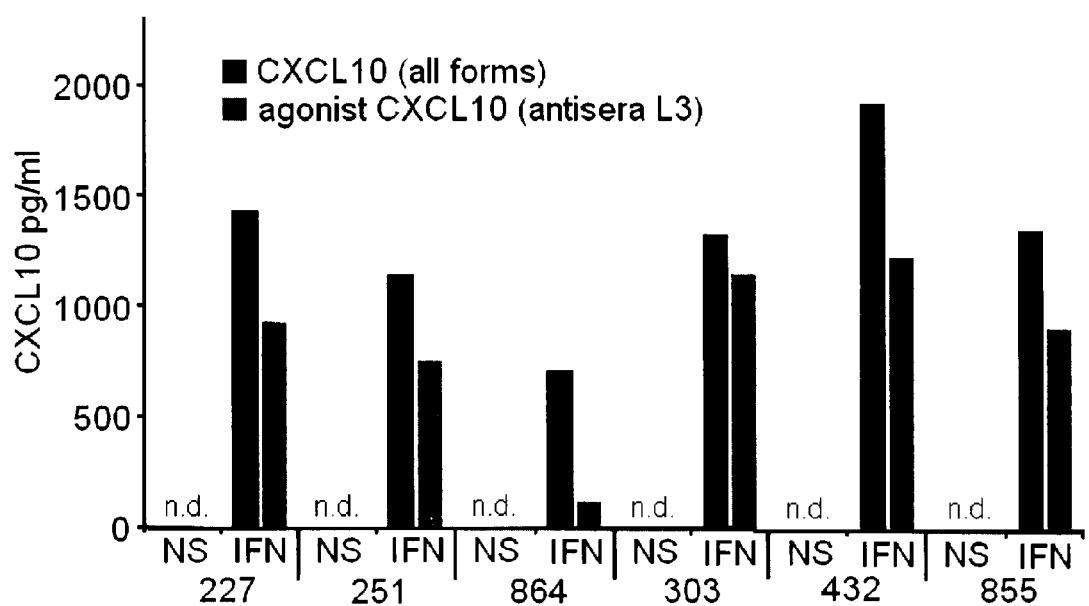
Figure 12C:
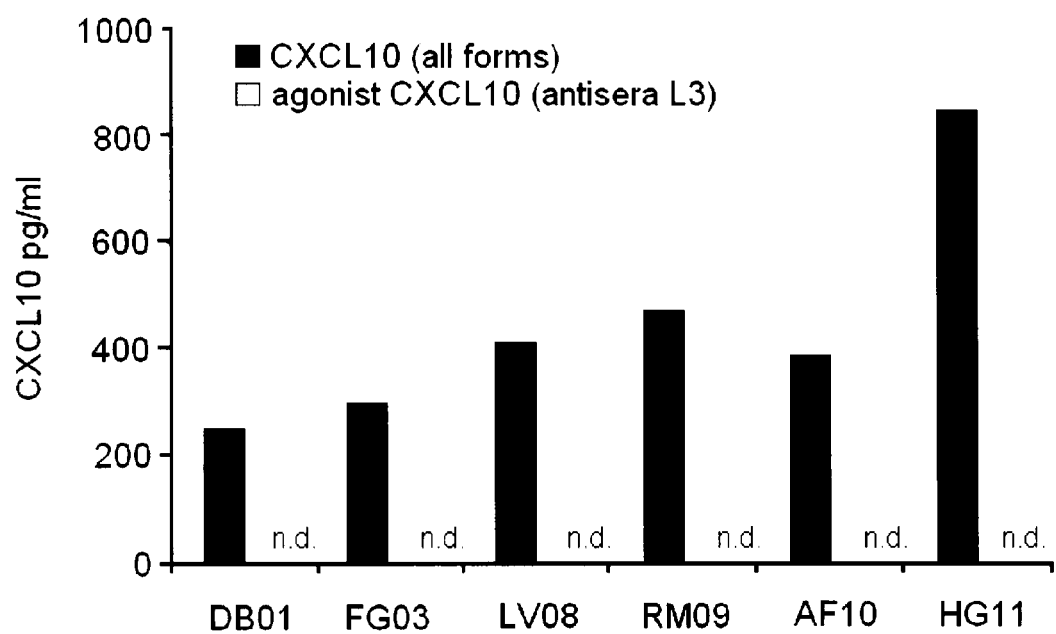
Figure 12D:
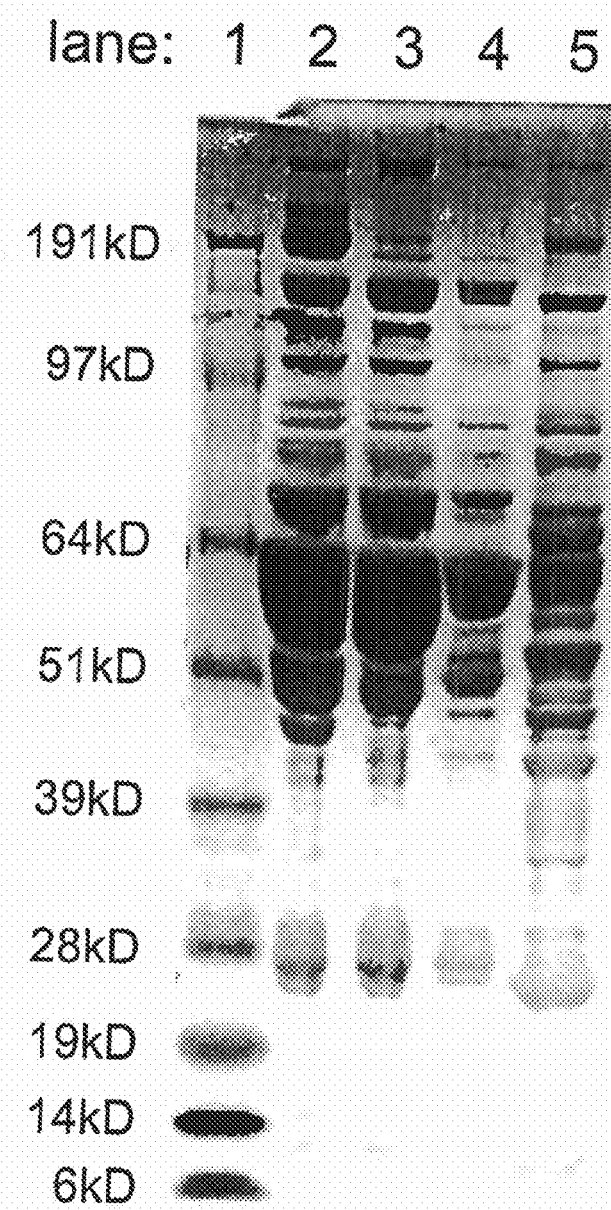
Figure 12E:
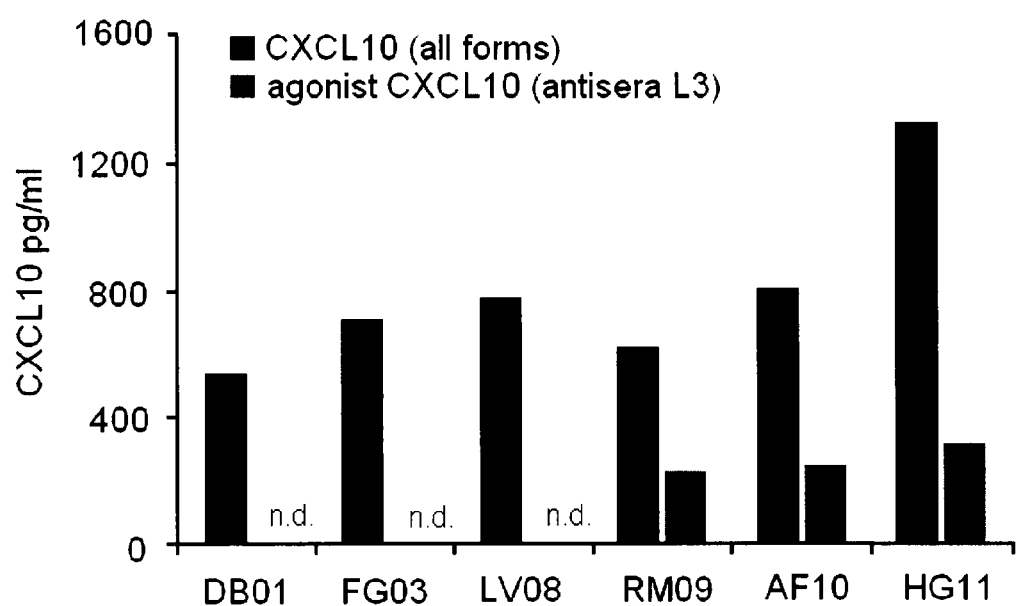
Figure 12F:
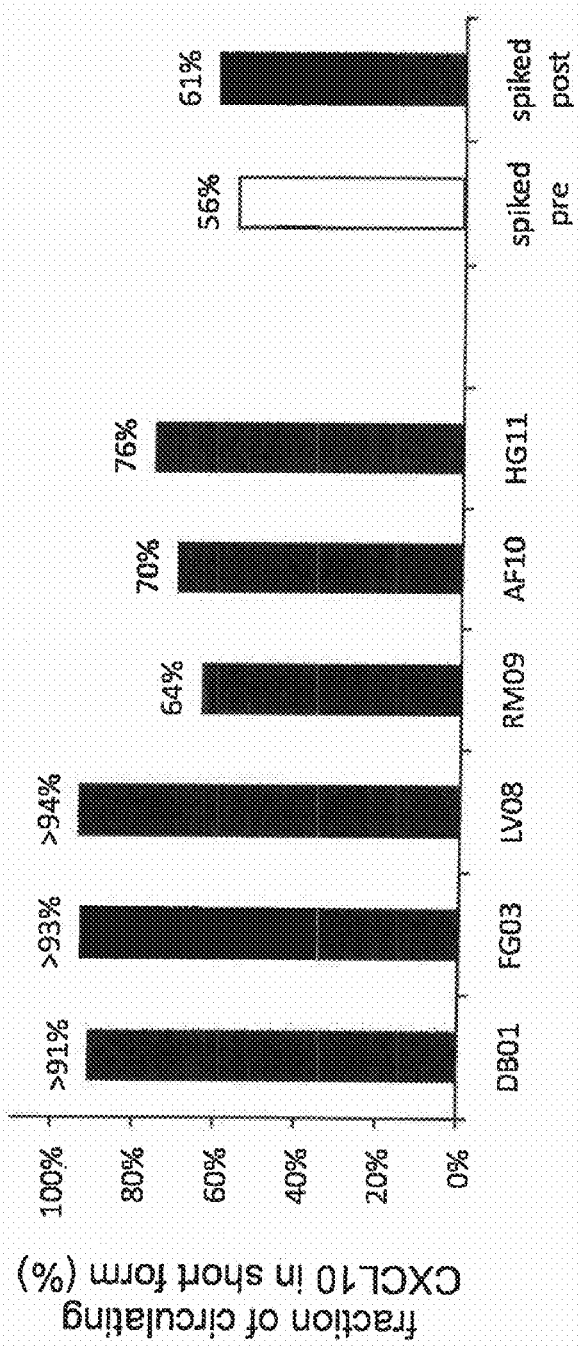
Figure 13A:
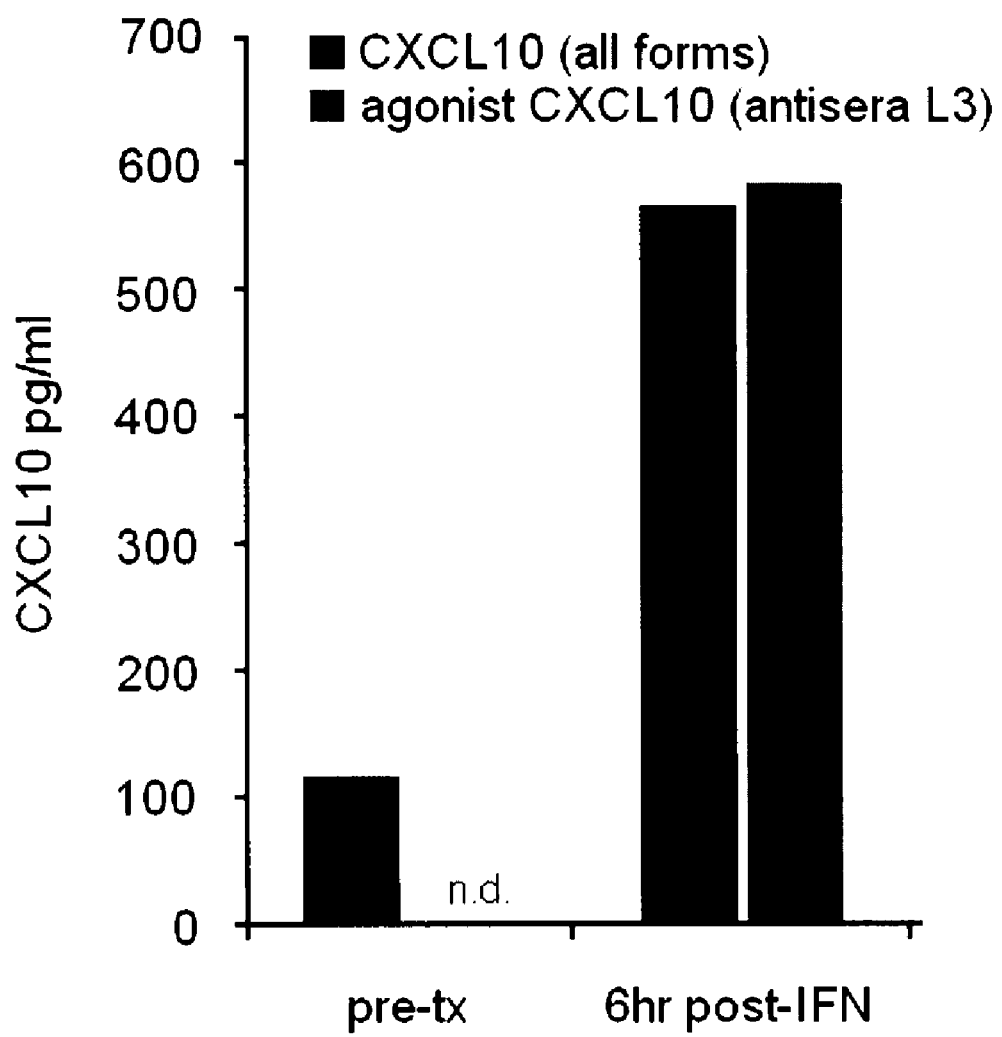
FIG. 13(A-C) shows the establishment of an 'in vivo bioassay' for agonist activity of plasma CXCL10.
Figure 13B:
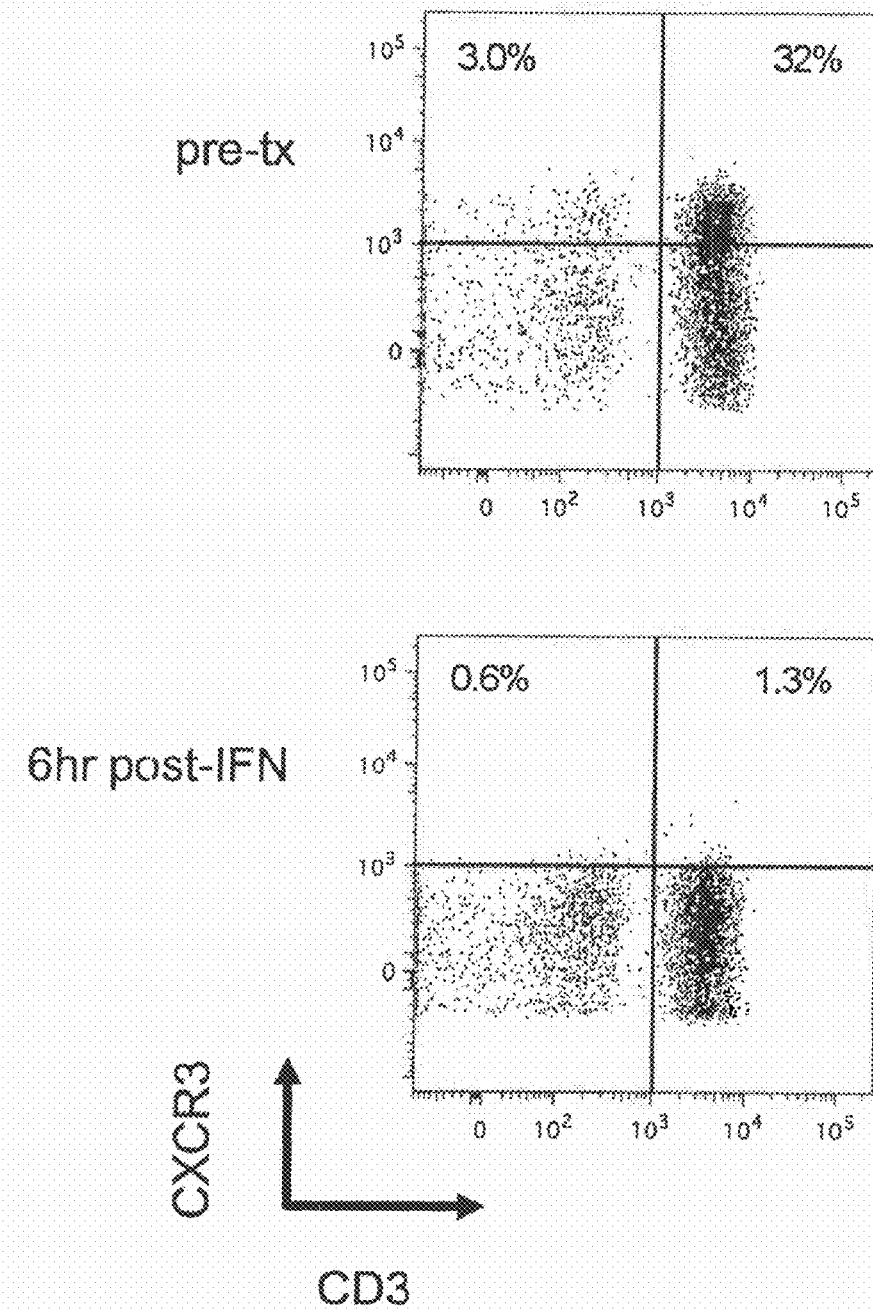
Figure 13C:
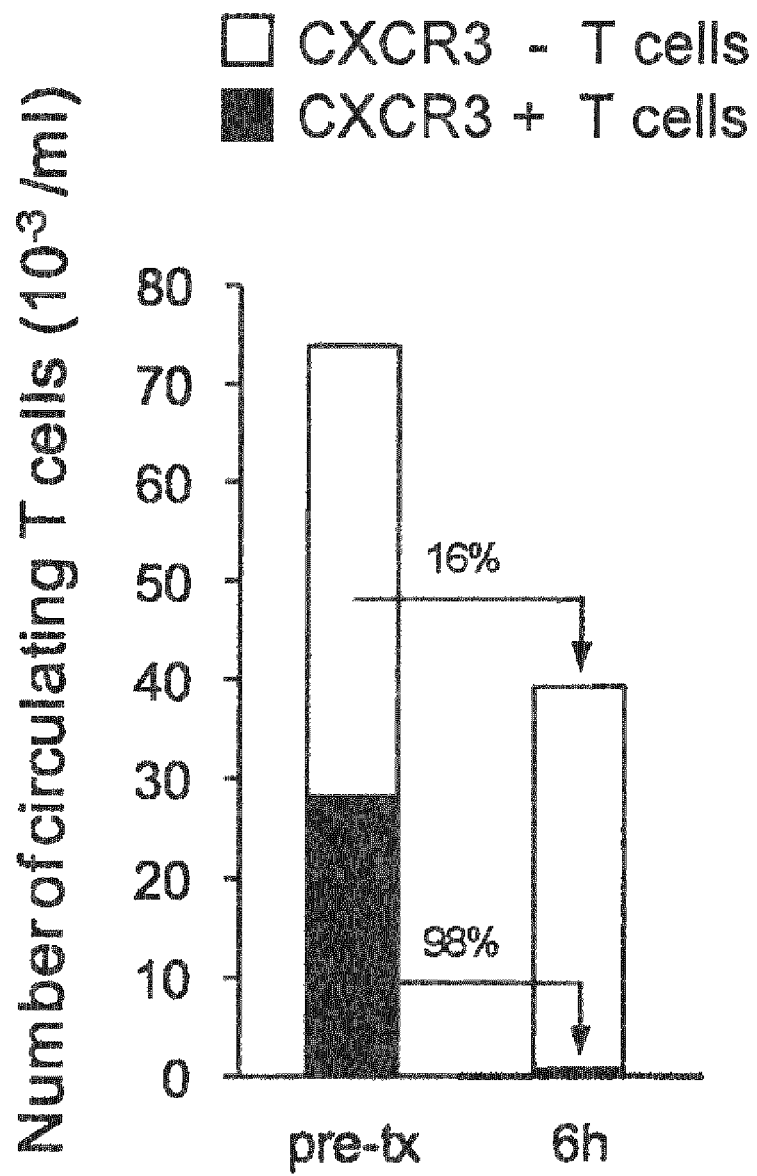

To overcome this hurdle, the inventors have generated antibodies capable of distinguishing the agonist form of CXCL10 (1-77) (see the Examples for details on the generation of the pAb specific for the NHz-terminal tail of the protein, termed antisera L3) (FIG. 12A, 12B). The ability to detect agonist CXCL10 permitted the inventors to test their hypothesis of chemokine antagonism in two ways. First, the inventors have evaluated six chronic HCV patients with elevated levels of plasma CXCL10. Blood collections were performed using P700 tubes (Becton Dickonson, CA, USA), which contain a DPP inhibitor thus preventing extra-corporeal cleavage of CXCL10. Patient plasma was isolated and using paired ELISA assays, we determined the concentration of total CXCL10 and agonist CXCL10 (FIG. 13C). While these results suggested in situ CXCL10 cleavage, the inventors were concerned by the relatively high limit of detection for the assay (see FIG. 12A). In order to be more confident in the results, the inventors have concentrated the patient plasma. Several strategies were evaluated with the Bio-Rad Proteominer System™ providing the most reproducible results. Briefly, patient plasma samples were passed over a column containing a combinatorial library of hexapeptides bound to beads. After saturating the available binding sites, high abundant proteins pass through the column, allowing for enrichment and concentration of less abundant proteins (FIG. 12D). We confirmed that CXCL10 was not saturating the available binding sites at the plasma volumes used, and we estimated the effective enrichment of the samples to be between 2-3×. After concentration, it was possible to detect agonist CXCL10 in three of the six patients (FIG. 12E). Using 50 pg/ml as the limit of the assay (based on ~2.5× concentration), the inventors calculated the fraction of CXCL10 that exists in 16 an NHz-truncated form (FIG. 12F) (FIG. 13F). To confirm that the inventors did not introduce a bias in the ratio of agonist CXCL10: cleaved CXCL10 during the enrichment protocol, the inventors have conducted spiking experiments using an equal mixture of CXCL1O (1-77) and CXCL1O (3-77), diluted into the plasma from a healthy donor (baseline plasma CXCL10 was undetectable in the donor plasma used). Pre- vs. post-concentration ratios were found to be similar (FIG. 12F).

CXCL10 Levels in Chronic HCV Patients Correlate with High Frequency of Circulating $CXCR3^+$ Cells As a second test for the inventors' hypothesis, the inventors have developed an 'in vivo-bioassay' to evaluate the fate of $CXCR3^+$ cells in individuals who have high levels of plasma CXCL10. To the inventors' knowledge, there is no report that evaluated in vivo migration as a function of plasma chemokine expression while taking care to determine that the chemokine is in a bioactive form. To establish a positive control for the assay, blood samples were collected from chronic HCV patients during the initiation of their treatment with peg-IFN-$\alpha_2$/RBV. 6 hr following the initial dose of peg-IFN-$\alpha_2$, the inventors observed high levels of plasma CXCL10, all of which existed in the agonist form, based on detection with anti-CXCL10, antisera L3 (FIG. 13A). Notably, there was a marked decrease in the level of circulating $CXCR3^+$ cells (FIG. 13B, 35% pre-treatment→2% 6 hr post-injection of peg-IFN-$\alpha_2$). Based on the enumeration of T cells and the selective decrease in $CXCR3^+$ cells (FIG. 13C), the interpretation is that the IFN treatment results in agonist CXCL10 production and migration of the $CXCR3^+$ cells. Regardless of the mechanism, the inventors have demonstrate an important correlation between the presence of the agonist form CXCL10 and decreased frequency of $CXCR3^+$ cells in circulation.

Figure 14:
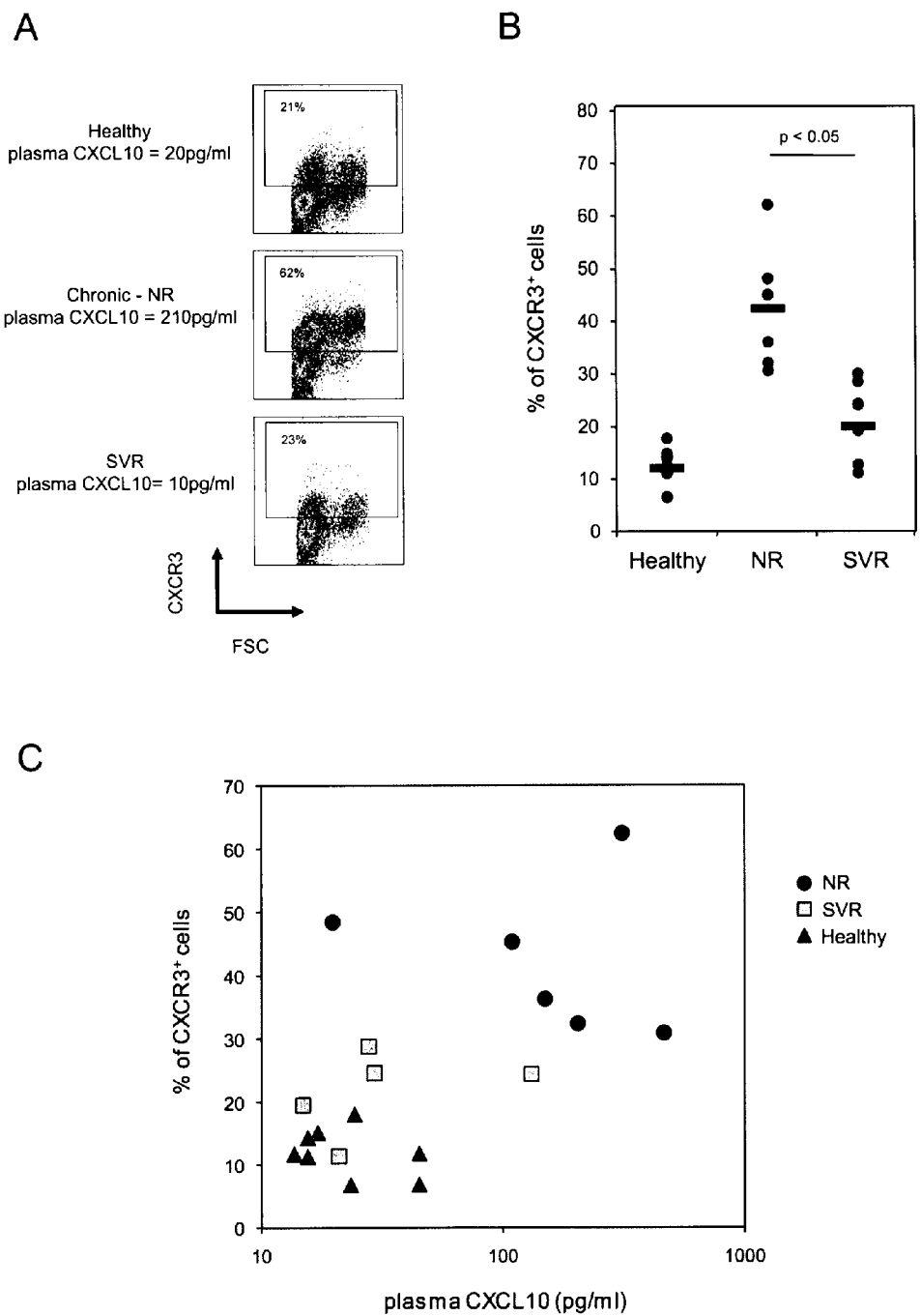
FIG. 14(A-C) shows a high frequency of $CXCR3^+$ cells in non-responders suggests that plasma CXCL10 is not bioactive.

Utilizing this in vivo-bioassay, the inventors next evaluated the frequency of circulating $CXCR3^+$ cells in chronic HCV patients (not receiving therapy). Strikingly, the inventors have found a higher frequency of $CXCR3^+$ cells in HCV non-responders, the same population with high plasma CXCL10 (FIG. 14A-C). Together, the data in FIGS. 12-14 suggests that plasma CXCL10 in chronic HCV patients exists in a modified but still immuno-reactive form, correlating with a high level of circulating $CXCR3^+$ cells.

Detection of the $NH_2$-Terminal Neo-Epitope of CXCL10

To provide direct evidence for in situ CXCL10 cleavage, the inventors have generated antibodies specific for the $NH_2$-terminus of CXCL10 (3-77) (see the Examples for details on the generation of mAb clone 52.1) (FIG. 15A). As shown, the inventors detected considerable amounts of plasma CXCL10 sensitive to the $NH_2$-terminal neo-epitope specific antibodies in two chronic HCV patients (PD05 and SF06, FIG. 15B white bars). As the assays utilize different capture antibodies, it is difficult to directly compare the amount of CXCL10 detected in the different ELISAs. Nonetheless, it is believed that all forms of circulating CXCL10 have not been accounted. Indeed, for many patient (including TM05), reactivity with anti-CXCL10, antisera L3 or clone 52.1 (FIG. 15B, white bars) have not been detected, yet plasma CXCL10 is present, based on assays that are not sensitive to the $NH_2$-terminus of the protein (FIG. 15B, black bars). One possibility is that upon $NH_2$-terminal cleavage, the protein becomes susceptible to other plasma and/or stromal proteases. For example, in vitro studies have shown serial cleavage of CXCL11, where DPP4 cleaves the penultimate X-Proline dipeptide followed by removal of the next $NH_2$-terminal amino acid by aminopepitidase N (APN or CD13) (30).

Elevated Dipeptidylpeptidase Activity in Chronic HCV Patients is Due to DPP4

There exist five enzymes with X-prolyl DPP activity, including DPP2, DPP4, DPP8, DPP9 and FAP (27). CXCL10 is a known substrate of DPP4, DPP8 and FAP. DPP4 is a membrane protein that may be shed upon inflammation (referred to as sDPP4) (31). In addition, several chemokines have been shown to be substrates for MMPs. CXCL10 has been reported to be cleaved at its C-terminus by MMP9 and MMP12 (25, 32); and it has been demonstrated that the cleavage product produced by MMP9 acting on CXCL10 remains an agonist for CXCR3 (25). One important and biologically relevant unknown is the action of MMP2 on CXCL10. Indeed, MMP2 has been shown to cleave the N-terminal amino acids of MCP-1 and SDF-1, thus generating an antagonist form of these molecules.

To evaluate the potential enzymes implicated in cleavage of CXCL10, the inventors exposed full length recombinant CXCL10 to active MMP2, MMP9 and DPP4. As predicted, MMP9 cleaved 9 amino acids from CXCL10 (FIG. 16A); and assaying for the $NH_2$-terminal residues using anti-CXCL3 antisera L3, we determined that MMP9 would be an unlikely candidate for generating in vivo the antagonist form of CXCL10 (FIG. 16B). MMP2 did not alter the mass of CXCL10 (FIG. 16A) and it also remained sensitive to antisera L3. As a positive control, DPP4 was used, which cleaved two amino acids from the $NH_2$-terminus, confirmed by mass analysis and the generation of a neo-epitope that was recognized by anti-CXCL10 clone 52.1 but not antisera L3.

To further investigate the mechanism of CXCL10 cleavage, the plasma DPP activity in patients with HCV infection has been assayed. Indeed, the plasma DPP activity was higher in chronic non-responders as compared to SVR and healthy individuals (FIG. 17A). Using a tri-peptide, broad-spectrum X-prolyl DPP inhibitor, isoleucine-proline-isoleucine (IPI) it was possible to inhibit >98% of the enzymatic activity; and treatment of the plasma with a DPP4-specific inhibitor, sitagliptin, defined sDPP4 as the enzyme likely to be responsible for the in vivo cleavage of CXCL10 (FIG. 7A). Due to elevated plasma levels of TIMP-1, the analysis of MMP activity has not been considered, but plasma concentrations of MMP2 and MMP9 in patients support that DPP4 is the in vivo candidate for the $NH_2$-terminal cleavage of CXCL10 (FIG. 19).

Interestingly, when the plasma concentration of CXCL10 and sDPP4 against each other was plotted, there was a positive correlation ($r_s$=0.6, FIG. 20A). Both molecules may be expressed by hepatocytes, and chronic inflammation and liver injury may be a common trigger for their expression (FIGS. 20B, 20C). A relativity plot of CXCL10, sDPP4, DPP activity, ALT and AST indicates such a correlation in chronic HCV patients but not SVR (FIG. 17B).

DISCUSSION

Chemokine Antagonism in Chronic HCV Patients

In a screen to identify correlates for treatment induced clearance, the inventors have re-discovered plasma CXCL10 as a pre-treatment negative prognostic marker in chronic HCV (FIG. 11). That such a chemokine is a negative predictor is somewhat counter-intuitive—instead, CXCL10 should facilitate recruitment of CXCR3$^+$ cells (activated $T_H1$, CD8$^+$ T and NK cells) to the infected liver (the source of the CXCL10) and participate in the efficient clearance of HCV by attracting activated lymphocytes. Herein, the inventors have explained why CXCL10 fails to assist in HCV clearance, and provide evidence that it in fact participates in the mechanism of treatment failure. Using reagents specific for the agonist form of CXCL10, the inventors have offered two lines of evidence for in vivo cleavage of CXCL10. First, the inventors have shown that the plasma CXCL10 present in chronic HCV patients exists primarily is a state that cannot be recognized by the $NH_2$-terminus CXCL10-specific pAb antisera L3 (FIG. 12). Second, the inventors have shown that high levels of plasma CXCL10 correlates with a high frequency of circulating CXCR3$^+$ cells (FIG. 14A-C). While there remain additional unknowns concerning the in situ cleavage of CXCL10, the inventors have demonstrated X-prolyl dipeptidylpeptidase activity based on the presence in some chronic HCV patients of CXCL10 lacking the two $NH_2$-terminal amino acids (FIG. 15). This data is supported by the failure of MMP2 and MMP9 to generate $NH_2$-terminal truncation of CXCL10 (FIG. 16); and by the higher levels of DPP4 activity in patients who failed pegylated IFN/Ribavirin therapy (FIG. 17).

The described studies offer the first evidence for chemokine antagonism as a possible mechanism in HCV disease pathogenesis. Although some pieces to this puzzle have been known, however, a synthetic evaluation of the problem has not been previously reported. Several independent studies have shown CXCL10 to be a negative predictive marker for response to therapy in chronic HCV patients (10-13). This observation has held up for genotype 1 and 4 patients (12), including difficult to treat patients with high levels of liver fibrosis, co-infected HIV/HCV infected patients and individuals with autoimmune sequella (e.g. mixed cryoglobulinemia and thyroiditis). Regarding CXCL10 being a substrate for DPP4, the seminal in vitro studies were performed by Proost and Van Damme, who established that CXCL10 (3-77) is capable of acting as a dominant negative, binding CXCR3 without signaling and competitively inhibiting binding by the agonist form of CXCL10 (1-77) (29). DPP4 is constitutively expressed by a wide range of cell types including hepatocytes, fibroblasts, epithelial and endothelial cells; and it is an activation marker for lymphocytes, in particular Th1 and effector/memory CD8$^+$ T cells. In addition to the cell associated DPP4, the enzyme is shed via the action of a still unidentified sheddase, and healthy donors harbor a physiologic plasma activity in a range of 12-25 U/L. While published kinetic studies suggest that this should be sufficient to cleave even high concentrations of CXCL10, no prior in vivo studies have confirmed CXCL10 to be present in an $NH_2$-terminus cleaved form. Finally, there have been two clinical reports that have made a link between dipeptidylpeptidases and chronic HCV. Firneisz et al. noted the link between liver injury and DPP activity and in a large 144 person cohort reported higher plasma X-prolyl dipeptidylpeptidase activity in patients with chronic HCV infection than in healthy controls (33). This study, however, did not define the enzyme responsible for the enzymatic activity, nor did it make a link to any of the immunologic or metabolic findings in chronic HCV patients. Yang evaluated sDPP4 as a marker of Th1 cell activation and followed 33 chronic HCV patients, reporting lower sDPP4 plasma concentrations as compared to healthy donors (34). Their study, however, did not take precautions to control for DPP4 shedding, nor did it evaluate enzymatic activity. Thus, it is believe that the study described herein, through the application of novel tools, has offered a synthetic picture and an important perspective regarding the inflammatory state of chronic HCV patients.

DPP4 Provides a Link Between Metabolic and Immunologic Dysregulation in chronic HCV Patients Insulin resistance and type II diabetes are common co-morbidities in chronic hepatitis C patients, with recent estimates indicating that 30-50% of patients have some degree of metabolic glucose abnormality. The incretin hormone, glucagon-like peptide-1 (GLP-1) enhances the release of insulin from islet β cells in a glucose-dependant manner. It also facilitates uptake of glucose by myocytes and hepatocytes while simultaneously suppressing glucagon secretion. GLP-1 has come under close scrutiny as a contributor to insulin resistance, and the mechanism is linked to cleavage by DPP4 (35). In fact, GLP-1 is the most characterized substrate of DPP4, and as the inventors have observed for agonist CXCL10, removal of the two N-terminal amino acids of GLP-1 converts it from an agonist to an antagonist.

It is worthy of mention that insulin resistance is a negative predictor for response to IFN/ribavirin therapy (36, 37). There is also a case report of a diabetic chronic HCV patients who received a 48 wk course of IFN/ribavirin and was cured of their type II diabetes (37). One possible explanation that might account for such a finding is that HCV-driven liver inflammation results in increase DPP4 activity that in turn revealed a predilection for type II diabetes. While not currently focused on DPP4, recent clinical studies have aimed at stabilizing patients' glucose control as a means of improving their response to therapy. These initial trials have failed, but perhaps they were utilizing the wrong anti-hyperglycemic agent(s).

DPP4 as a Novel Drug Target for the Treatment of Chronic HCV

Following from the clinical use of recombinant GLP-1 as a means of enhancing insulin production and more recently from the biochemical evidence that GLP-1 is cleaved by DPP4 into an antagonist form that results in insulin resistance, many biotechnology groups and pharmaceutical companies have made an effort to develop DPP4-specific inhibitors as a novel treatment for type-2 diabetes. DPP4 inhibition prevents the inactivation of glucagon-like peptide I (GLP-1), resulting in increased endogenous levels of agonist GLP-1. Sitagliptin (Merck; approved by the FDA in 2007) and Vildagliptin (Novartis; approved by the FDA in 2009) are orally active compounds with a long duration, and both have been used as monotherapy with excellent safety profiles and seem to be well tolerated with minimal risk of hypoglycaemia or weight gain. DPP4 inhibitors are quickly being phased in as first-line treatment of type II diabetes.

The identification of agonist CXCL10 as an in vivo target for DPP4 and the possibility that this cleavage event is a mechanism of treatment failure in chronic HCV patients are attractive. As such, DPP4 inhibition are beneficial for HCV patients, with the objective being restoration of the chemokine gradient and the ability of CXCR3$^+$ cells to properly traffic to sites of inflammation. Not only can we envision DPP4-inhibition enhancing clearance rates achieved by peg-IFN-$\alpha_2$/ribavirin therapy, but it offers the added benefit of addressing underlying metabolic problems present within the same patient population.

Pharmaceutical Applications

As used herein, "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions. If necessary, the chimeric compounds can be co-administered with a solubilizing agent, such as cyclodextran.

A pharmaceutical composition is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerin, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., chimericompounds) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Nucleic acid molecules encoding the chimeric compounds of the invention can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al. (1994) PNAS 91:3054-3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells that produce the gene delivery system.

The dosages can be assessed by the physician administrating the therapy taking into consideration factors such as weight, age, sex, race, severity of the infection and other prior, concurrent and/or future therapies.

EXAMPLES

Material and Methods

Reagents:

Human recombinant IP10 was provided by Abcam and Peprotech

Recombinant CD26 was provided by Alexis or Sigma

Monoclonal (clone 33036) and Goat polyclonal anti-IP10 antibodies were obtained from R&D Systems.

Luminex reagents were provided by Biosource.

Luminex technology. The luminex technology allows us to follow up to 25 analytes in a single plasma sample. It is a bead based sandwich ELISA that utilizes cytometric principles and permits the simultaneous analysis of up to 100 analytes while using a small amount of patient plasma or cell supernatent.

Flow cytometry. Thawed PBMCs from patients were stained with CXCR3-PE and CD19-fitc (BD) for 20 min. Cells were washed, fixed with 1% PFA and read on FACS-CALIBUR (BD).

IP-10 AA sequence

Pro-IP-10: mnqtailicc lifltlsgiq gvplsrtvrc tcisisnqpv nprsleklei ipasqfcprv eiiatmkkkg ekrclnpesk aiknllkavs kemskrsp (SEQ ID NO: 1).

Secreted full length protein: vplsrtvrc tcisisnqpv nprsleklei ipasqfcprv eiiatmkkkg ekrclnpesk aiknllkavs kemskrsp (SEQ ID NO:2).

Cleavage product after CD26 treatment, as reported in literature:

```
                                          (SEQ ID NO: 3)
_LSRTVRC TCISISNQPV NPRSLEKLEI IPASQFCPRV

EIIATMKKKG EKRCLNPESK AIKNLLKAVS KEMSKRSP.
```

In vitro cleavage of IP10:

100 ug of IP 10 were incubated with 0.25 U of recombinant CD26 in a 100 mM Tris-HCL pH 8 solution, for 2 h at 37° C., in 100 ul final volume. The cleavage was controlled by spotting 1 ul of the digested product in a H4 protein chip array and analyzed by SELDI-TOF (Ciphergen mass spectrometry technology).

Western Blot:

Recombinant IP10 samples, treated or not with CD26 were run in a 15% bis-acryalmide gel. We used 48 cm plates and 1 mm spacer, and run the gel in tris-tricine buffer. Proteins were transferred to Hybond-P membrane (Amersham Biosciences) by a semi-dry western blot transfer procedure (EBU-4000 CBS-scientific Co). The membrane was saturated with TBS-1% tween-20-1% BSA solution. Revelation was done with the monoclonal antibody 33036 incubated O/N at 4° C. in the saturation buffer. 3 Washes step were performed with TBS-1% Tween at RT. Detection was done with anti-Mouse IgG (H+L) coupled to HRP (Vector laboratories). After 3 washes step, the ECL plus detection system (Amersham) was used for blot revelation.

We used SeeBlue Plus™ prestained standard (Invitrogen) as molecular weight markers.

Mass spectrometry conditions: 3 µl of 0.5 mg/ml monoclonal antibody (33036 clone) were added to the spots of a preactivated ProteinChip array (PS10; Ciphergen Biosystems). The PS10 array consists of a surface with carbonyldiimidazole moieties that dock proteins by covalently reacting with their amine groups. The arrays were incubated overnight at 4° C. in a humidified chamber. After blocking residual active sites (with 2×5 µl of ethanolamine 1M pH 8 for 15 min at RT). The arrays were assembled into a deep-well-type Bioprocessor assembly, then washed once, 10 min, with 200 µl PBS-0.5% triton-X100 and twice, 3 min, with PBS. The arrays were then incubated with 100 ul of PBS-0.1% Triton X-100 containing the recombinant IP 10 protein at RT during for 1 h30 on a shaker, then washed 3-times with 150 µl of PBS. After rinsing with 1 mM HEPES, the arrays were removed from the Bioprocessor assembly and air-dried. The following energy-absorbing molecules (EAMs) was used: sinapinic acid saturated in 1:1 acetonitrile/0.5% aqueous TFA (SPA). Two 0.5-µl aliquots of EAM solution were applied to the spot surface, and the sample was allowed to dry.

The ProteinChip arrays were analyzed in the ProteinChip System Series 4000 (Ciphergen). The range of molecular weights (MWs) investigated was from 0 to 20,000. The focus mass was set at 8.5 kDa. The data were analyzed using CiphergenExpress Software.

Generation of rabbit polyclonal anti-LIP10 antibodies: Production of polyclonal anti-long form IP10 antibodies was generated by Proteogenix company (Alsace, France): the VPLSRTVRC (SEC ID NO:5) peptide (corresponding of the $NH_2$ terminal of the full-length IP-10 protein of SEQ ID NO:2), corresponding to the NH2 peptidic sequence of Human IP-10, was synthesized and coupled to KLH. 5 New Zealand White rabbits were bled, and pre-immune serum was collected before the immunization. After immunization, the specific immunoglobulins production was tested bleeding rabbits; sera titrations were done by direct Elisa: the plate was coated with the same peptide as used for the immunization. After a 90 days immunization protocol, Rabbit IgG were purified: first by an affinity column containing the VPLSRTVRC (SEC ID NO:5) peptide, then a depletion step was achieved by a second affinity column containing the shorter peptide LSRTVRC (SEQ ID NO:6) (corresponding to the IP-10 shared peptidic sequence and the $NH_2$ terminal of the full-length IP-10 protein of SEQ ID NO:2) to remove the non specific IgG.

Sandwich ELISA to Quantify TOTAL and L-IP10:

Maxisorp plate (Nunc) were coated with 2 ug/ml of Monoclonal antibody (33036) in PBS O/N at 4° C. The wells were saturated with 200 ul PBS-0.05% Tween-20-1% BSA1 to 2 h at RT. Samples were diluted ¼ or ⅒ in saturation buffer and incubated at RT for 2 h. A standard curve was obtained by diluting recombinant IP10, truncated or not by CD26 before use, in the same solution used for saturation. Each experiment was duplicated in the same plate. For secondary revelation we used the biotinylated goat polyclonal antibody (Total IP10, 0.25 ug/ml final concentration) and Rabbit polyclonal anti-VPL (long IP10, 2 ug/ml final concentration) (incubation 1H30 at RT) in the same plate.

For the last step revelation, we used HRP-streptavidin (BD Pharmingen) for the goat polyclonal and HRP-goat anti-rabbit IgG (H+L), mouse and human adsorbed (Southern Biotech) for the rabbit polyclonal. After last wash step, 100 ul of TMB substrat (Sigma) were added to each well and 100 ul of HCl 1N to stop the reaction. Plates were read in a Labsystems Multiskan MS (Thermo) device.

For the ELISA our limit of detection is 50 pg/ml for total IP10 and 250 pg/ml for L-IP10.

Plasma Samples:

Healthy donors whole blood (EFS, Necker Paris France) was stimulated with Intron A, human recombinant interferon alpha 2 (Schering Plough): 1.5 ml whole blood was diluted with 1.5 ml of RPMI. Diluted blood was stimulated with 3000 to 10000 U/ml of IFNa during 20 h to 24 h at 37° C. Plasma were collected and stored between −20° and −80° C. until analysis by Elisa.

HCV plasma from Paris: Blood samples were collected from 21 HCV chronic patients (initially defined by a persistence of HCV in the plasma and elevated ALT) who previously received IFNα therapy. 13 patients responded to therapy and controlled the infection ("Responder") whereas 8 patients failed to respond to therapy ("non responder").

For each cohort, plasma were isolated, frozen and analyzed by Luminex technology.

For the ELISA discriminating total and long form IP10 in HCV patients we concentrated 10× the plasma by a vivaspin-2 system with a 3000 Da MW cut off membrane. Samples were diluted twice for the ELISA analysis.

Surface CXCR3 expression: Blood samples were collected from 12 HCV chronic patients (initially defined by a persistence of HCV in the plasma and elevated ALT) who previously received IFNα therapy. 6 patients responded to therapy and controlled the infection ("SVR") whereas 6 patients failed to respond to therapy ("Chronic"). PBMCs were isolated and frozen till further analysis. Thawed PBMCs were analyzed by flow cytometry to compare CXCR3 expression on different cell subsets. B cells were identified in PBMCs as CD19+ cells and CXCR3 expression was analyzed on their subset population.

sCD26 ELISA: human DPPIV/cd26 quantification in the plasma was performed with a Quantikine Immunoassay kit (R &D Systems). Samples were diluted 1/100 and tested in duplicate as manufactor instructions.

DPPIV activity in plasma sample: DPPIV activity was performed with DPPIV-Glo protease Assay (Promega). Briefly, in a white plate (Greiner bio-one), 50 ul of kit reagent (with luciferase substrate) were added to 50 µl plasma sample diluted in 10 mM Tris-HCl pH8-0.1% prionex (Calbiochem). Samples were tested in duplicate at different dilutions. Plates were read in a Microluminat LB (EG&G Berthold) device.

Additional Patient Samples

For multi-analyte profiling, MMP2, MMP9 and DPP assays, banked patient samples were obtained from prior collections performed by S. Pol. during the treatment and management of chronic HCV patients receiving peg-IFN-$\alpha_2$/ribivirin therapy. All patients had genotype 1 infection. Plasma samples were obtained pre-, during and post-treatment. Samples were stored at −80 prior to use. For analysis of agonist and $NH_2$-truncated forms of CXCL10, new collections were required so that blood samples could be collected in BD700 tubes (which contain a DPP4 inhibitor), thus preserving the circulating form of CXCL10. These samples were obtained as part of the study protocol RBM 03-59, approved by the INSERM clinical investigation department with ethical approval from the committee for the protection of persons (CPP) of Necker Hospital. HCV patients with chronic infection were defined by anti-HCV Abs and HCV RNA positivity for a period of time greater than six months. All patients had genotype 1 infection and were treated by a combination of peg-IFN-$\alpha_2$ and ribivirin for at least three month. Sustained virological responders (SVR) were defined as individuals absent of HCV RNA for longer than 6 months after termination of therapy. Protocols were reviewed and approved by local ethical committees and patients provided informed consent. The study protocols conformed to the ethical guidelines of the Declaration of Helsinki.

Multi-Analyte Profiling

Plasma were clarified by a high-speed centrifugation and analyzed using the Luminex xMAP technology. Samples were measured by a diagnostic lab, Rules Based Medicine for measurement of 83 molecules with all assays being CLIA certified (validated using guidelines set forth by the Clinical and Laboratory Standards Institute). The cut-off value was derived by determining the average of >200 normals and adding 3 standard deviations to the mean. The Least Detectable Dose (LDD) is the lower limit at which the system can accurately calculate the concentration of an experimental sample, having confidence that the concentration is higher than a blank sample. The LDD is determined by analyzing 20 blank samples, calculating the mean background, and adding 3 standard deviations to this mean. The Lower Assay Limit (LAL) is each assay's working sensitivity as defined by the lowest concentration calibrator found on the standard curve that provides a quantifiable measurement above background. The LAL is typically lower than the LDD. Analyte measurements reported below the LDD and above the LAL may be real values whose precision was examined closely. Values above the LDD possess excellent precision with coefficients of variation (CV) less than 10%. For data mining, values below the LAL were replaced with a value that is 50% of the lowest value measured in the data set. For all analytes used in this study, the LDD can be found in Table S3. In parallel, analytes not part of this multiplex screen (IFNα and CXCL10) were analyzed by Luminex, using commercially available kits (Invitrogen).

Generation of Agonist CXCL10 and $NH_2$-Truncated CXCL10 Specific pAbs

Production of polyclonal agonist CXCL10 specific antibodies were generated by Proteogenix company (Alsace, France). The $NH_2$-terminal 9 amino acids of the secreted form of CXCL10 (VPLSRTVRC) were synthesized and coupled to KLH. Eight New Zealand White rabbits were bled, and pre-immune serum was collected before the immunization. After immunization, anti-sera were tested by direct ELISA (plates were coated with the same peptide used for immunization). After a ninety days immunization protocol consisting of five injections, serum IgGs were subjected to an affinity column containing the VPLSRTVRC peptide, then a depletion column containing the short peptide (LSRTVRC, corresponding to $NH_2$-terminal 7 amino acids of DPP4 cleaved CXCL10). Two of the eight rabbits tested had high affinity and specific reactivity for agonist CXCL10 (1-77). IgG purification was performed and further tested. For these studies, we utilized the pAbs isolated from rabbit L3 (and called antisera L3), which after immunodepletion showed no binding to CXCL10 (3-77) (up to concentrations of 2 µg/ml) and has a limit of detection of 125 pg/ml for CXCL10 (1-77) in a sandwich ELISA. Concentration of patient plasma provided an assay with an effective limit of detection of 50 pg/ml. Additionally, we demonstrated lack of cross-reactivity with other α-chemokines (data not shown). Production of monoclonal single chain antibodies specific for the neo-epitope created by DPP4 cleavage of CXCL10 were generated by AbD Serotec (Dusseldorf, Germany). Briefly, peptide corresponding to the $NH_2$-terminal 7 amino acids of DPP4 cleaved CXCL10 (LSRTVRC) and peptide corresponding to the native protein (VPLSRTVRC) were conjugated to BSA and TRF. The HuCal library (Human Combinatorial Antibody Library) was screened first with the conjugated peptides coated in the ELISA plate, clones reactive for the neo-epitope and not the native peptide were then screened with the recombinant proteins (CXCL10 (3-77) and (1-77)). The clone 52.1 is specific of the neo-epitope and was used as the coating antibody for the sandwich ELISA specific of the antagonist form.

Assays for Discriminating Agonist CXCL10 and $NH_2$-Truncated CXCL10

To generate CXCL10 (3-77), recombinant human CXCL10 (Peprotech, Rocky Hill, N.Y. USA) was incubated with recombinant DPP4 (Sigma) in a 100 mM Tris-HCL pH 8 solution, for 2 h at 37° C. SELDI-TOF Mass spectrometry: 1 µl of the digested product was spotted onto an H4 protein chip. Arrays were incubated and washed as per manufacturers instructions and analyzed using the ProteinChip System Series 4000 (Ciphergen). The range of molecular weights (MWs) investigated was from 0 to 20,000 Da. The focus mass was set at 8.5 kDa. Data were analyzed using CiphergenExpress Software. Chemotaxis assays: Peripheral blood mononuclear cells were purified from healthy volunteers and treated with 1 mg/ml phytohemagglutinin for 3 days then 40 U/ml of recombinant hIL-2 (R&D Systems) was added for and additional 2 days prior to use of the cells. Lymphocyte chemotaxis was performed using 5 µm pore size Multiscreen-MIC plates (Milliopore). To monitor CXCL10 (1-77) or CXCL10 (3-77) directed migration, lymphocytes were added to the top chamber and chemokine was added to the bottom. Lymphocytes were allowed to migrate for 2 hours at 37° C. and cells in the bottom chamber were counted using a Guava cytometer (Guava Technologies, C A, USA). Calcium-flux assays: Increased intracellular $[Ca^{2+}]$ in response to CXCR3 signaling were monitored by FACS. Briefly, CHO-K1 cells were transfected with a plasmid encoding the full-length open reading frame of CXCR3 (generously provided by Dr. C P Tensen, Leiden, The Netherlands). Stably transfected cells were screened for CXCR3 expression (anti-human CXCR3 clone 1C6, Becton Dickinson) and loaded with Fura-3-AM. $Ca^{++}$ release was measured using a Canto II Cytometer. Baseline signal was collect prior to addition of chemokine. For competitive antagonist assessment, cells were first incubated for 5 min with CXCL10 (3-77) then exposed to CXCL10 (1-77). Sandwich ELISA. Maxisorp plates (Nunc) were coated with 2 □g/ml of the capture antibody—mAb anti-CXCL10 (clone 33036) in PBS overnight at 4° C. The wells were saturated with 200 µl 0.05% Tween-20, 1% BSA in PBS for 1-2 h at room temperature. Samples were diluted in saturation buffer and incubated at room temperature for 2 h. A standard curve was obtained by diluting recombinant CXCL10 (1-77) or CXCL10 (3-77). Each experiment was run in duplicate with two different detection antibodies—a commercially available goat pAb that recognized both forms of CXCL10 or a rabbit pAb (antisera L3) that is specific for the agonist form of CXCL10. For detection of the two amino acid $NH_2$-truncated form of CXCL10, we utilized the scAb (clone 52.1) as the capture reagent and goat pAb anti-CXCL10 for detection. Plates were read in a Labsystems Multiskan MS (Thermo) device.

Concentration of Patient Plasma

The ProteoMiner kit (Bio-Rad) was used as per manufacture's instructions. Briefly, the kit contains 100 µl of ProteoMiner beads in minispin columns. Human serum samples (1 ml) were applied to the columns. To ensure effective binding, columns were rotated for 2 hr at room temperature prior to washing away unbound proteins with PBS. To elute bound proteins, the columns were treated 2 times with 100 µl of an acidic urea/CHAPS buffer. Collected fractions were neutralized with 15 µl of 2M sodium carbonate and desalted used a Zeba spin column (Pierce).

FIG. 11. Multi-analyte profiling of chronic HCV patients reveals CXCL10 as a negative predictor for response to therapy. (A) Patient plasma was obtained prior to initiation of treatment and subjected to multi-analyte profiling. Kruskal-Wallis analysis of variance, comparing patients who failed to respond to therapy (non-responders, N–n=9), those who cleared the virus (sustained virologic responders, S–n=13) and healthy individuals (H–n=7) revealed 13 analytes that distinguish the groups with a p<0.01 (indicated by *). (B) Data for four chemokines are shown over the kinetic course of treatment. Black circles, treatment non-responders; Grey squares, sustained virologic responders. p<0.01 indicated by *.

FIG. 12. Evidence for NH$_2$-terminal truncation of CXCL10 in chronic HCV patients. (A) To establish a sandwich ELISA assay for CXCL10 (1-77) we coated plates with the mouse anti-human CXCL10 mAb (clone 33036A), which captures both forms of CXCL10. A standard curve was established to determine the specificity and limit of detection of the detection antibody, rabbit anti-human CXCL10 (antisera L3) pAb. Serial dilution of human recombinant CXCL10 (1-77) (red) and CXCL10 (3-77) (black) was utilized. (B) Whole blood from six healthy donors (donor number is indicated) was collected in heparin tubes. Whole blood was incubated overnight in the absence (non-stimulated, NS) or presence of IFN□$_2$ (IFN). Samples were analyzed in parallel sandwich ELISA assays, as described in materiel and methods for detection of total CXCL10 (black) and agonist form of CXCL10 (red). (C) Plasma was isolated from six HCV chronic non-responder patients, using P700 tubes (Becton Dickinson) in order to protect the circulating form of CXCL10. As above plasma concentrations of total CXCL10 and agonist CXCL10 was determined. (D) To concentrate patient samples, the Proteominer System™ was utilized according to manufacturers instructions. A representative blot is shown to demonstrate the concentration of less abundant plasma proteins. 1 ml of a plasma sample was treated and 15 □g of protein was used in each lane. Lane 1, pre-stained molecular weight markers; lane 2, patient plasma; lane 3, flowthrough from the column; lane 4, wash; lane 5, elution fraction. Analyzis was performed using SDS-PAGE and the gel was stained with Coomassie blue. (E) Plasma samples from (C) were concentrated using the Proteominer System™ and re-analyzed. n.d.=not detected. (F) Taking 50 pg/ml as the limit of the assay following ~2.5× concentration, the fraction of CXCL10 that exists in an NH$_2$-truncated form was calculated. Spiked samples were utilized as a control for the effects of sample concentration.

FIG. 13. Establishment of an 'in vivo bio-assay' for agonist activity of plasma CXCL10. Plasma and whole blood was collected from an HCV chronic patient prior to initiation of treatment and six hours after the first dose of IFNα$_2$. The plasma was analyzed by parallel sandwich ELISA for detection of total CXCL10 (black) and agonist CXCL10 (red) (A). FACS analysis using CXCR3 and CD3 specific antibodies and Tru-count tubes containing lineage markers was performed, to determine the percentage of CXCR3$^+$ cells in circulation (B), and to calculate their absolute number (C), respectively.

FIG. 14. High frequency of CXCR3$^+$ cells in non-responders suggests that plasma CXCL10 is not bio-active. (A, B) Cell profiling studies were performed on chronic non-responders (NR), sustained virologic responders (SVR) and healthy individuals to determine the circulating levels of CXCR3$^+$ cells. Representative FACS plots are shown with the corresponding plasma concentration of total CXCL10 (A). Data from all groups are shown with each filled circle representing a single individual (B). Data from the same patients were plotted against the plasma concentration of total CXCL10 (C).

FIG. 15. Detection of NH$_2$-truncated CXCL10 in chronic HCV patients. (A) To establish a sandwich ELISA assay for NH$_2$-truncated CXCL10 (3-77) we coated plates with the anti-human CXCL10 mAb (clone 52.1), which captures the NH$_2$-truncated form of CXCL10. A standard curve was established with recombinant protein CXCL10 (3-77) and reactivity to CXCL10 (1-77) was tested. The limit of detection for the assay is 25 pg/ml. (B) Plasma of three chronic HCV non-responders were run in duplicate to assess concentration of total (black bars) and NH$_2$-truncated CXCL10 (white bars). Plasma of a healthy donor was spiked with a ratio of 1:1 of recombinant CXCL10 (1-77) and (3-77). Data is representative of replicate experiments.

Figure 16:
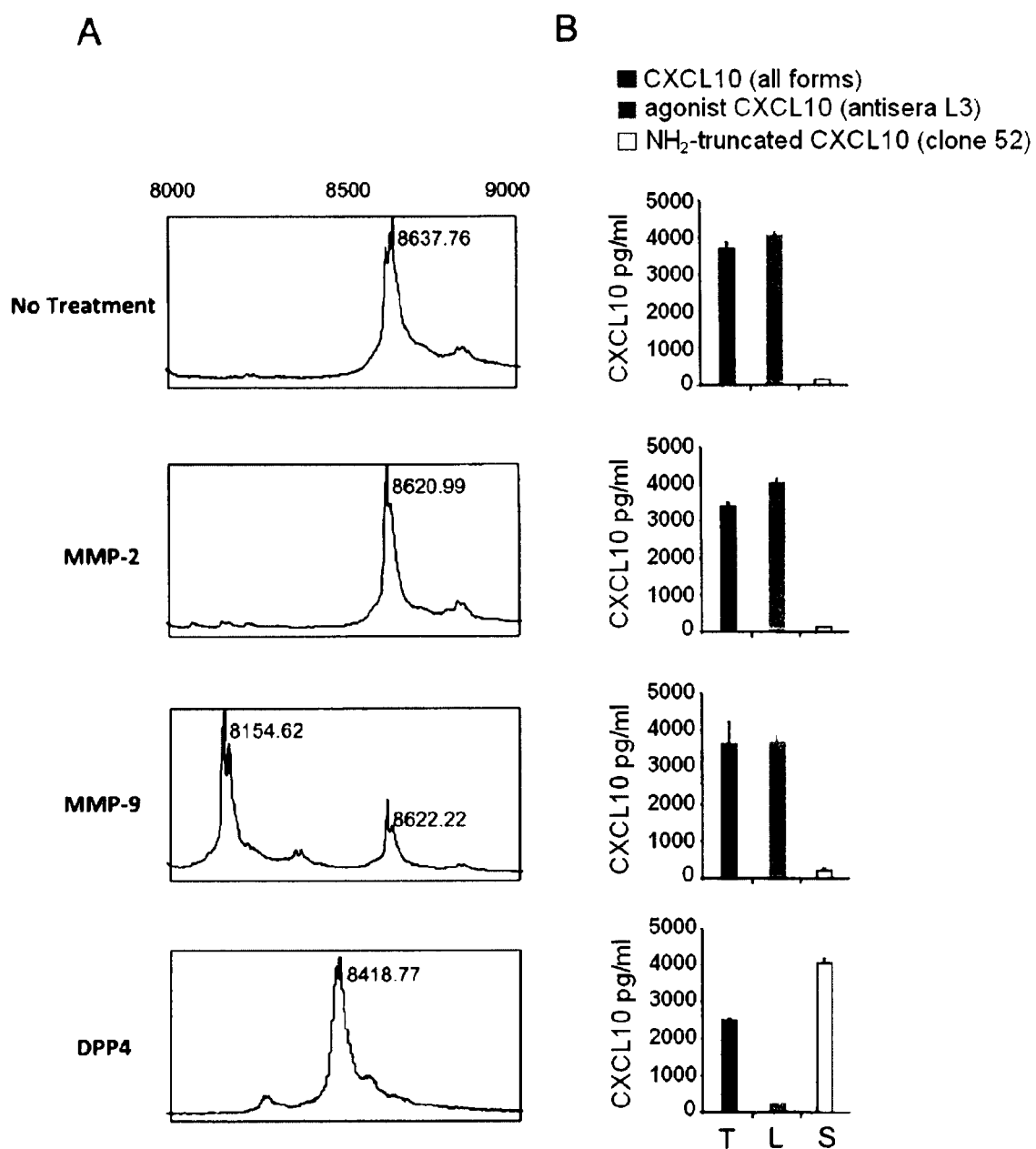
FIG. 16(A-B) shows that DPP4 but not MMP2 or MMP9 cleavage results in $NH_2$-terminal truncation of CXCL10.

FIG. 16. DPP4 but not MMP2 or MMP9 cleavage results in NH$_2$-terminal truncation of CXCL10. Human recombinant CXCL10 (1-77) was digested in vitro with MMP-2 and MMP-9 as described in material and method. (A) 200 ng of the digestion were spotted in a H4 array and analyzed by SELDI-TOF. (B) CXCL10 exposed to MMP-2, MMP-9 and DPP4 were run in three parallel ELISA assays to determine the relative percent of total protein (T, black bars) that is present in the agonistic long form (L, red bars) or NH$_2$-truncated short form (S, white bars).

FIG. 17. Elevated X-prolyl dipeptidylpeptidase activity in chronic HCV patients is mediated by DPP4. (A) The activity of DPP4 was measured using a luciferase based assay—DPP4-Glo protease Assay (Promega). Plasma from chronic non-responders (NR), sustained virologic responders (SVR) and healthy donors were tested in the presence or absence of the pan-DPP inhibitor IPI, and the DPP4 specific inhibitors sitagliptin. The ratio of RLU (relative light units) of sample/RLU of PBS is represented with each dot being the average of replicate wells for a single individual. This experiment is representative of two independent assays. (B) A relativity network is diagrammed indicating the correlation between DPP activity, sDPP4 plasma concentration, total CXCL10 plasma concentration and the liver enzymes ALT and AST. A spearman correlation matrix was used to determine the correlation coefficient. Lines indicate correlations >0.5 with a heat map indicating the strength of the correlation. For all correlations shown the p<0.05. Additional details may be found in supplementary FIG. 3.

FIG. 18. The X-prolyl dipeptidylpeptidase DPP4 cleaves the two N-terminal amino acids of CXCL10, generating the antagonist CXCL10 (3-77) form. (A) Human recombinant CXCL10 (1-77) was digested in vitro with recombinant DPP4 to obtain CXCL10 (3-77). 0.5 µg were spotted in an H4 column for mass spectrometry analysis. The molecular weight difference (red number) between CXCL10 (1-77) and CXCL10 (3-77) is 0.2 KDa, corresponding to a 2 amino-acid difference. (B) Human PHA-T blasts were placed into the top well of Corning migration chambers with increasing concentrations of CXCL10 (1-77) (red) or CXCL10 (3-77) (black) in the bottom chamber. The absolute number of migrated cells was determine using a Guava cytometer with values represented. Each bar is the mean of duplicate wells and error bars indicate one standard deviation of the mean. This experiment is representative of results obtained with 3 different healthy donors. (C) CHO-K1 cells were stably transfected with a plasmid expressing human CXCR3. FACS confirmation is shown with cell stained using an anti-CXCR3 mAB. (D) Fura-3-AM fluorescent dye labeled CXCR3-expressing CHO cells were used for Ca$^{++}$ flux experiments. Arrows indicate the injection of the stimulant. In the first plot, CXCL10 (1-77) was used. In the second plot, CXCL10 (3-77) was used. And in the third plot, cells were first incubated at room temperature for 5 min with CXCL10 (3-77) (pre-tx) then followed by a stimulation with CXCL10 (1-77). Data is representative of 3 independent experiments.

FIG. 19. Plasma concentration of MMP2 and MMP9 in patients with chronic HCV. (A, B) The plasma concentration of MMP2 (A) and MMP9 (B) was measured using luminex technology. Plasma from chronic non-responders (NR), patients who achieved a sustained virologic response (SVR)

and healthy donors, were tested. Each patient is represented with the median indicated by a black bar. Comparison between groups using a two-tailed U-test revealed no statistically significant differences for either analyte.

FIG. 20. Plasma concentration of sDPP4 and CXCL10 correlate with elevated liver enzymes in patients with chronic HCV. (A-C) Plasma levels of sDPP4 and CXCL10 are plotted against ALT and AST levels. Spearman correlation coefficients are reported.

REFERENCES

1. Houghton, M., and Abrignani, S. 2005. Prospects for a vaccine against the hepatitis C virus. *Nature* 436:961-966.
2. Bowen, D. G., and Walker, C. M. 2005. Adaptive immune responses in acute and chronic hepatitis C virus infection. *Nature* 436:946-952.
3. Cooper, S., Erickson, A. L., Adams, E. J., Kansopon, J., Weiner, A. J., Chien, D. Y., Houghton, M., Parham, P., and Walker, C. M. 1999. Analysis of a successful immune response against hepatitis C virus. *Immunity* 10:439-449.
4. Lechner, F., Wong, D. K., Dunbar, P. R., Chapman, R., Chung, R. T., Dohrenwend, P., Robbins, G., Phillips, R., Klenerman, P., and Walker, B. D. 2000. Analysis of successful immune responses in persons infected with hepatitis C virus. *J Exp Med* 191:1499-1512.
5. Khakoo, S. I., Thio, C. L., Martin, M. P., Brooks, C. R., Gao, X., Astemborski, J., Cheng, J., Goedert, J. J., Vlahov, D., Hilgartner, M., et al. 2004. HLA and NK cell inhibitory receptor genes in resolving hepatitis C virus infection. *Science* 305:872-874.
6. Feld, J. J., and Hoofnagle, J. H. 2005. Mechanism of action of interferon and ribavirin in treatment of hepatitis C. *Nature* 436:967-972.
7. Luster, A. D., and Ravetch, J. V. 1987. Biochemical characterization of a gamma interferon-inducible cytokine (IP-10). *J Exp Med* 166:1084-1097.
8. Singh, U. P., Singh, S., Taub, D. D., and Lillard, J. W., Jr. 2003. Inhibition of IFN-gamma-inducible protein-10 abrogates colitis in IL-10-/- mice. *J Immunol* 171:1401-1406.
9. Rhode, A., Pauza, M. E., Barral, A. M., Rodrigo, E., Oldstone, M. B., von Herrath, M. G., and Christen, U. 2005. Islet-specific expression of CXCL10 causes spontaneous islet infiltration and accelerates diabetes development. *J Immunol* 175:3516-3524.
10. Butera, D., Marukian, S., Iwamaye, A. E., Hembrador, E., Chambers, T. J., Di Bisceglie, A. M., Charles, E. D., Talal, A. H., Jacobson, I. M., Rice, C. M., et al. 2005. Plasma chemokine levels correlate with the outcome of antiviral therapy in patients with hepatitis C. *Blood* 106:1175-1182.
11. Lagging, M., Romero, A. I., Westin, J., Norkrans, G., Dhillon, A. P., Pawlotsky, J. M., Zeuzem, S., von Wagner, M., Negro, F., Schalm, S. W., et al. 2006. IP-10 predicts viral response and therapeutic outcome in difficult-to-treat patients with HCV genotype 1 infection. *Hepatology* 44:1617-1625.
12. Romero, A. I., Lagging, M., Westin, J., Dhillon, A. P., Dustin, L. B., Pawlotsky, J. M., Neumann, A. U., Ferrari, C., Missale, G., Haagmans, B. L., et al. 2006. Interferon (IFN)-gamma-inducible protein-10: association with histological results, viral kinetics, and outcome during treatment with pegylated IFN-alpha 2a and ribavirin for chronic hepatitis C virus infection. *J Infect Dis* 194:895-903.
13. Diago, M., Castellano, G., Garcia-Samaniego, J., Perez, C., Fernandez, I., Romero, M., Iacono, O. L., and Garcia-Monzon, C. 2006. Association of pretreatment serum interferon gamma inducible protein 10 levels with sustained virological response to peginterferon plus ribavirin therapy in genotype 1 infected patients with chronic hepatitis C. *Gut* 55:374-379.
14. Roe, B., Coughlan, S., Hassan, J., Grogan, A., Farrell, G., Norris, S., Bergin, C., and Hall, W. W. 2007. Elevated serum levels of interferon-gamma-inducible protein-10 in patients coinfected with hepatitis C virus and HIV. *J Infect Dis* 196:1053-1057.
15. Zeremski, M., Markatou, M., Brown, Q. B., Dorante, G., Cunningham-Rundles, S., and Talal, A. H. 2007. Interferon gamma-inducible protein 10: a predictive marker of successful treatment response in hepatitis C virus/HIV-coinfected patients. *J Acquir Immune Defic Syndr* 45:262-268.
16. Antonelli, A., Ferri, C., Fallahi, P., Ferrari, S. M., Frascerra, S., Carpi, A., Nicolini, A., and Ferrannini, E. 2008. Alpha-chemokine CXCL10 and beta-chemokine CCL2 serum levels in patients with hepatitis C-associated cryoglobulinemia in the presence or absence of autoimmune thyroiditis. *Metabolism* 57:1270-1277.
17. McQuibban, G. A., Gong, J. H., Tam, E. M., McCulloch, C. A., Clark-Lewis, I., and Overall, C.M. 2000. Inflammation dampened by gelatinase A cleavage of monocyte chemoattractant protein-3. *Science* 289:1202-1206.
18. Zhang, K., McQuibban, G. A., Silva, C., Butler, G. S., Johnston, J. B., Holden, J., Clark-Lewis, I., Overall, C. M., and Power, C. 2003. HIV-induced metalloproteinase processing of the chemokine stromal cell derived factor-1 causes neurodegeneration. *Nat Neurosci* 6:1064-1071.
19. Dinarello, C. A. 2000. Interleukin-18, a proinflammatory cytokine. *Eur Cytokine Netw* 11:483-486.
20. Kaplanski, G., Farnarier, C., Payan, M. J., Bongrand, P., and Durand, J. M. 1997. Increased levels of soluble adhesion molecules in the serum of patients with hepatitis C. Correlation with cytokine concentrations and liver inflammation and fibrosis. *Dig Dis Sci* 42:2277-2284.
21. Zaman, A., Rosen, H. R., Ingram, K., Corless, C. L., Oh, E., and Smith, K. 2007. Assessment of FIBROSpect II to detect hepatic fibrosis in chronic hepatitis C patients. *Am J Med* 120:280 e289-214.
22. Thimme, R., Bukh, J., Spangenberg, H. C., Wieland, S., Pemberton, J., Steiger, C., Govindarajan, S., Purcell, R. H., and Chisari, F. V. 2002. Viral and immunological determinants of hepatitis C virus clearance, persistence, and disease. *Proc Natl Acad Sci USA* 99:15661-15668.
23. Boker, K. H., Pehle, B., Steinmetz, C., Breitenstein, K., Bahr, M., and Lichtinghagen, R. 2000. Tissue inhibitors of metalloproteinases in liver and serum/plasma in chronic active hepatitis C and HCV-induced cirrhosis. *Hepatogastroenterology* 47:812-819.
24. Schwartz, T. W., Frimurer, T. M., Holst, B., Rosenkilde, M. M., and Elling, C. E. 2006. Molecular mechanism of 7™ receptor activation—a global toggle switch model. *Annu Rev Pharmacol Toxicol* 46:481-519.
25. Van den Steen, P. E., Husson, S. J., Proost, P., Van Damme, J., and Opdenakker, G. 2003. Carboxyterminal cleavage of the chemokines MIG and IP-10 by gelatinase B and neutrophil collagenase. *Biochem Biophys Res Commun* 310:889-896.
26. Loos, T., Mortier, A., Gouwy, M., Ronsse, I., Put, W., Lenaerts, J. P., Van Damme, J., and Proost, P. 2008. Citrullination of CXCL10 and CXCL11 by peptidylarginine deiminase: a naturally occurring posttranslational modification of chemokines and new dimension of immunoregulation. *Blood* 112:2648-2656.
27. Gorrell, M. D. 2005. Dipeptidyl peptidase IV and related enzymes in cell biology and liver disorders. *Clin Sci (Lond)* 108:277-292.

28. Ludwig, A., Schiemann, F., Mentlein, R., Lindner, B., and Brandt, E. 2002. Dipeptidyl peptidase IV (CD26) on T cells cleaves the CXC chemokine CXCL11 (I-TAC) and abolishes the stimulating but not the desensitizing potential of the chemokine. *J Leukoc Biol* 72:183-191.
29. Proost, P., Schutyser, E., Menten, P., Struyf, S., Wuyts, A., Opdenakker, G., Detheux, M., Parmentier, M., Durinx, C., Lambeir, A. M., et al. 2001. Amino-terminal truncation of CXCR3 agonists impairs receptor signaling and lymphocyte chemotaxis, while preserving antiangiogenic properties. *Blood* 98:3554-3561.
30. Proost, P., Mortier, A., Loos, T., Vandercappellen, J., Gouwy, M., Ronsse, I., Schutyser, E., Put, W., Parmentier, M., Struyf, S., et al. 2007. Proteolytic processing of CXCL11 by CD13/aminopeptidase N impairs CXCR3 and CXCR7 binding and signaling and reduces lymphocyte and endothelial cell migration. *Blood* 110:37-44.
31. Bauvois, B. 2004. Transmembrane proteases in cell growth and invasion: new contributors to angiogenesis? *Oncogene* 23:317-329.
32. Cox, J. H., Dean, R. A., Roberts, C. R., and Overall, C. M. 2008. Matrix metalloproteinase processing of CXCL11/I-TAC results in loss of chemoattractant activity and altered glycosaminoglycan binding. *J Biol Chem* 283:19389-19399.
33. Firneisz, G., Lakatos, P. L., and Szalay, F. 2001. Serum dipeptidyl peptidase IV (DPP IV, CD26) activity in chronic hepatitis C. *Scand J Gastroenterol* 36:877-880.
34. Yang, S. S., Fu, L. S., Chang, C. S., Yeh, H. Z., Chen, G. H., and Kao, J. H. 2006. Changes of soluble CD26 and CD30 levels correlate with response to interferon plus ribavirin therapy in patients with chronic hepatitis C. *J Gastroenterol Hepatol* 21:1789-1793.
35. Chowdhury, T. A., and Hossain, B. 2007. New drugs for the treatment of type 2 diabetes. *Br J Hosp Med (Lond)* 68:178-183.
36. Negro, F. 2006. Insulin resistance and HCV: will new knowledge modify clinical management? *J Hepatol* 45:514-519.
37. Romero-Gomez, M. 2006. Insulin resistance and hepatitis C. *World J Gastroenterol* 12:7075-7080.

The invention claimed is:

1. A method of monitoring the necessity for administering a CD26 inhibitor to a patient who is in need of receiving an effective amount of a CD26 inhibitor, the method comprises:
   recovering samples from the patient and a control, wherein the control is at least one control selected from a healthy individual and a patient having cleared infection,
   inactivating the intrinsic dipeptidylpeptidase IV (DPPIV),
   detecting levels of a long form of interferon-gamma induced protein-10 (IP-10), which is a full length form of a secreted bioactivated IP-10 with 77 amino acids, and a short form of IP-10 (sIP-10), which is a N-terminal truncated antagonist of the long form of IP-10 lacking 2 or 4 amino acids from the N-terminus of the long form of IP-10, in the patient and control, and
   comparing the levels and ratios of sIP-10 and the long form of IP-10, wherein an elevated level of antagonist forms of IP-10 (sIP-10) relatively to the level of the long form of IP-10 in the patient indicates the necessity of administering a CD26 inhibitor.

2. The method of claim 1, wherein the sample is a plasma or serum sample.

3. The method of claim 1, wherein the patient is a patient chronically infected with HCV.

4. The method of claim 1, wherein the long IP-10 form comprises the amino acid sequence of SEQ ID NO: 2.

5. The method of claim 1, wherein sIP-10 comprises the amino acid sequence of SEQ ID NO: 3.

6. The method of claim 1, wherein sIP-10 comprises the amino acid sequence of SEQ ID NO: 4.

7. The method of claim 1, wherein the long IP-10 form consists of the amino acid sequence of SEQ ID NO: 2.

8. The method of claim 1, wherein sIP-10 consists of the amino acid sequence of SEQ ID NO: 3.

9. The method of claim 1, wherein sIP-10 consists of the amino acid sequence of SEQ ID NO: 4.

10. A method of monitoring the necessity for administering a CD26 inhibitor to a patient who is in need of receiving an effective amount of a CD26 inhibitor, the method comprises:
    recovering samples from the patient and a control, wherein the control is selected from a healthy individual and/or a patient having cleared infection,
    inactivating the intrinsic dipeptidylpeptidase IV (DPPIV),
    detecting levels of a long form of interferon-gamma induced protein-10 (IP-10), which is a full length form of a secreted bioactivated IP-10 and a short form of IP-10 (sIP-10), which is a N-terminal truncated antagonist of the long form of IP-10 lacking 2 or more amino acids from the N-terminus of the long form of IP-10, in the patient and control, and
    comparing the levels and ratios of sIP-10 and the long form of IP-10, wherein an elevated level of sIP-10 relatively to the level of the long form of IP-10 in the patient indicates the necessity of administering a CD26 inhibitor.

* * * * *